US011896234B2

(12) United States Patent
Fojtik et al.

(10) Patent No.: US 11,896,234 B2
(45) Date of Patent: Feb. 13, 2024

(54) APPARATUS AND METHOD OF USING IN SITU SOLIDIFYING COMPLEX COACERVATES FOR VASCULAR OCCLUSION

(71) Applicant: FLUIDX MEDICAL TECHNOLOGY, LLC, Salt Lake City, UT (US)

(72) Inventors: Shawn Patrick Fojtik, Park City, UT (US); Russell Stewart, Salt Lake City, UT (US)

(73) Assignee: Fluidx Medical Technology, LLC, Salt Lake City, UT (US)

( * ) Notice: Subject to any disclaimer, the term of this patent is extended or adjusted under 35 U.S.C. 154(b) by 870 days.

(21) Appl. No.: 16/964,424

(22) PCT Filed: Jan. 25, 2019

(86) PCT No.: PCT/US2019/015127
§ 371 (c)(1),
(2) Date: Jul. 23, 2020

(87) PCT Pub. No.: WO2019/147922
PCT Pub. Date: Aug. 1, 2019

(65) Prior Publication Data
US 2021/0045748 A1 Feb. 18, 2021

Related U.S. Application Data

(60) Provisional application No. 62/622,195, filed on Jan. 26, 2018.

(51) Int. Cl.
| A61B 17/12 | (2006.01) |
| A61L 24/00 | (2006.01) |
| A61L 24/04 | (2006.01) |
| A61L 24/10 | (2006.01) |
| C08F 220/34 | (2006.01) |
| C08F 220/56 | (2006.01) |
| C08L 79/02 | (2006.01) |
| A61B 17/00 | (2006.01) |

(52) U.S. Cl.
CPC .. *A61B 17/12109* (2013.01); *A61B 17/12031* (2013.01); *A61B 17/12136* (2013.01); *A61B 17/12195* (2013.01); *A61L 24/0015* (2013.01); *A61L 24/0042* (2013.01); *A61L 24/046* (2013.01); *A61L 24/108* (2013.01); *C08F 220/34* (2013.01); *C08F 220/56* (2013.01); *C08L 79/02* (2013.01); *A61B 2017/00893* (2013.01); *A61B 2017/1205* (2013.01); *A61L 2300/254* (2013.01); *A61L 2300/256* (2013.01); *A61L 2300/41* (2013.01); *A61L 2300/416* (2013.01); *A61L 2430/36* (2013.01)

(58) Field of Classification Search
None
See application file for complete search history.

(56) References Cited

U.S. PATENT DOCUMENTS

| 3,458,460 | A | 7/1969 | Shepard et al. |
| 3,947,396 | A | 3/1976 | Kangas et al. |
| 3,950,296 | A | 4/1976 | Kangas et al. |
| 4,767,463 | A | 8/1988 | Brode et al. |
| 4,913,743 | A | 4/1990 | Brode et al. |
| 5,529,914 | A | 6/1996 | Hubbell et al. |
| 6,312,725 | B1 | 11/2001 | Wallace et al. |
| 6,428,978 | B1 | 8/2002 | Olsen et al. |
| 6,497,729 | B1 | 12/2002 | Moussey et al. |
| 6,568,398 | B2 | 5/2003 | Cohen |
| 6,916,488 | B1 | 7/2005 | Meier et al. |
| 6,921,380 | B1 | 7/2005 | Epstein et al. |
| 7,622,533 | B2 | 11/2009 | Lee |
| 8,283,384 | B2 | 10/2012 | Stewart et al. |
| 9,173,971 | B2 | 11/2015 | Stewart |
| 9,272,069 | B2 | 3/2016 | Stewart et al. |
| 9,421,300 | B2 | 8/2016 | Stewart |
| 9,913,927 | B2 | 3/2018 | Stewart |
| 2001/0016577 | A1 | 8/2001 | Dobrozsi et al. |
| 2001/0056301 | A1 | 12/2001 | Goupil et al. |
| 2002/0006886 | A1 | 1/2002 | Beerse et al. |
| 2002/0164364 | A1 | 11/2002 | Quong |
| 2002/0169476 | A1 | 11/2002 | Cohen |
| 2003/0023000 | A1 | 1/2003 | Bavouzet |

(Continued)

FOREIGN PATENT DOCUMENTS

| CN | 1341032 | 3/2002 |
| CN | 1446590 | 10/2003 |

(Continued)

OTHER PUBLICATIONS

Japanese Office Action for Appln. No. 2020-561602 dated Nov. 2, 2022.
U.S. Appl. No. 16/450,338, U.S. Pat. No. 10,729,807.
U.S. Appl. No. 15/880,650, U.S. Pat. No. 10,369,249.
U.S. Appl. No. 15/131,583, U.S. Pat. No. 9,867,899.
U.S. Appl. No. 15/833,157, U.S. Pat. No. 10,653,813.

(Continued)

*Primary Examiner* — Patricia Duffy
*Assistant Examiner* — Garen Gotfredson
(74) *Attorney, Agent, or Firm* — Thomas Horstemeyer, LLP

(57) ABSTRACT

Described herein are the use of fluid complex coacervates that produce solid adhesives in situ to anchor medical devices such as catheters in a blood vessel. The anchored devices permit the targeted delivery of bioactive agents. The anchored devices can perform as an embolic agent by reducing or preventing blood flow in the vessel. Additionally, the embolic produced from the solid adhesive produced in situ can also include one or more bioactive agents that can be released in a controlled manner.

20 Claims, 8 Drawing Sheets

(56) References Cited

U.S. PATENT DOCUMENTS

| | | | |
|---|---|---|---|
| 2004/0013738 A1 | 1/2004 | Voigt et al. |
| 2004/0086479 A1 | 5/2004 | Grinstaff et al. |
| 2004/0013832 A1 | 7/2004 | Hubbell et al. |
| 2004/0138329 A1 | 7/2004 | Hubbell et al. |
| 2004/0208845 A1 | 10/2004 | Michal et al. |
| 2005/0019262 A1 | 1/2005 | Chernomorsky et al. |
| 2005/0020734 A1 | 1/2005 | Asgarzadeh et al. |
| 2005/0147580 A1 | 7/2005 | Connor et al. |
| 2005/0220751 A1 | 10/2005 | Charmot et al. |
| 2005/0281883 A1 | 12/2005 | Daniloff et al. |
| 2006/0007528 A1 | 1/2006 | Cao et al. |
| 2006/0015083 A1 | 1/2006 | Munro et al. |
| 2006/0039950 A1 | 2/2006 | Zhou et al. |
| 2006/0073207 A1 | 4/2006 | Masters et al. |
| 2006/0116682 A1 | 6/2006 | Longo |
| 2006/0122290 A1 | 6/2006 | Hubbell et al. |
| 2006/0156954 A1 | 7/2006 | Li et al. |
| 2006/0183848 A1 | 8/2006 | Maier et al. |
| 2006/0240064 A9 | 10/2006 | Hunter et al. |
| 2006/0241242 A1 | 10/2006 | Devlin |
| 2006/0275337 A1 | 12/2006 | Cohen Stuart et al. |
| 2006/0276371 A1 | 12/2006 | Schreiner et al. |
| 2007/0020469 A1 | 1/2007 | Wood et al. |
| 2007/0077276 A1 | 4/2007 | Haynie |
| 2007/0085059 A1 | 4/2007 | Mora-Gutierrez et al. |
| 2007/0191273 A1 | 8/2007 | Ambati et al. |
| 2007/0196454 A1 | 8/2007 | Stockman et al. |
| 2008/0003288 A1 | 1/2008 | Bromberg et al. |
| 2008/0075778 A1 | 3/2008 | Heller |
| 2008/0084000 A1 | 4/2008 | Forster |
| 2009/0054927 A1 | 2/2009 | Agnew |
| 2009/0162407 A1 | 6/2009 | Biggs et al. |
| 2009/0214660 A1 | 8/2009 | Vasconcellos et al. |
| 2010/0021574 A1 | 1/2010 | Laguna Granja et al. |
| 2010/0040688 A1 | 2/2010 | Elbert et al. |
| 2010/0056474 A1 | 3/2010 | Baker et al. |
| 2010/0120923 A1 | 5/2010 | Stewart et al. |
| 2010/0143351 A1 | 6/2010 | Fyfe et al. |
| 2010/0215748 A1 | 8/2010 | Ladet et al. |
| 2010/0291169 A1 | 11/2010 | Toreki et al. |
| 2010/0305626 A1 | 12/2010 | Stewart et al. |
| 2011/0054392 A1 | 3/2011 | Nies |
| 2011/0287067 A1 | 11/2011 | Stewart |
| 2011/0288274 A1 | 11/2011 | Russell et al. |
| 2012/0177918 A1 | 7/2012 | Stewart |
| 2013/0129787 A1 | 5/2013 | Stewart |
| 2013/0189313 A1 | 7/2013 | Stewart et al. |
| 2013/0336917 A1 | 12/2013 | Cruise |
| 2014/0287061 A1 | 9/2014 | Landolina |
| 2016/0007451 A1 | 1/2016 | Tomikawa et al. |
| 2016/0011028 A1 | 1/2016 | Stewart |
| 2016/0074516 A1 | 3/2016 | Lapitsky et al. |
| 2016/0074556 A1 | 3/2016 | Stewart et al. |
| 2016/0250375 A1 | 9/2016 | Stewart |
| 2017/0157285 A1 | 6/2017 | Stewart |

FOREIGN PATENT DOCUMENTS

| | | |
|---|---|---|
| CN | 101405037 | 4/2009 |
| CN | 106474530 | 3/2017 |
| DE | 19810965 | 9/1999 |
| EP | 0632329 | 12/1997 |
| JP | 2003280056 | 12/1991 |
| JP | 2002166158 | 6/2002 |
| JP | 2002538848 A | 11/2002 |
| JP | 2009084224 | 4/2009 |
| JP | 2009084292 | 4/2009 |
| JP | 2017529118 A | 10/2017 |
| WO | 1995006056 | 3/1995 |
| WO | 200018469 A1 | 4/2000 |
| WO | 2000043050 A1 | 7/2000 |
| WO | 2002092217 | 11/2002 |
| WO | 2002100453 | 12/2002 |
| WO | 2005018421 | 3/2005 |
| WO | 2006120557 | 3/2007 |
| WO | 2007024972 | 3/2007 |
| WO | 2007030811 | 3/2007 |
| WO | 2009094060 | 7/2009 |
| WO | 2011011658 | 1/2011 |
| WO | 2011028967 | 3/2011 |
| WO | 2011106595 | 8/2011 |
| WO | 2011149907 | 12/2011 |
| WO | 2012065148 | 5/2012 |
| WO | 2013003400 | 1/2013 |
| WO | 2016011028 | 1/2016 |
| WO | 2017152039 | 9/2017 |

OTHER PUBLICATIONS

U.S. Appl. No. 15/325,885, U.S. Pat. No. 9,913,927.
U.S. Appl. No. 12/864,045, U.S. Pat. No. 9,272,069.
U.S. Appl. No. 12/508,280, U.S. Pat. No. 8,283,384.
U.S. Appl. No. 13/617,882, U.S. Pat. No. 9,913,926.
U.S. Appl. No. 15/918,423, U.S. Pat. No. 10,517,987.
U.S. Appl. No. 16/912,830, US-2020-0324017-A1.
International Search Report for PCT/US19/15127 dated Aug. 27, 2019.
International Search Report and Written Opinion for PCT/US2019/15127 dated Aug. 27, 2019.
International Search Report and Written Opinion for PCT/US2015/040377 dated Oct. 13, 2015, 16pp.
International Search Report and Written Opinion for PCT/US2018/058015 dated Feb. 6, 2019, 12pp.
International Search Report and Written Opinion for PCT/US2019/035923 daled Aug. 15, 2019, 35pp.
Treat et al., "Guanidine-containing methacrylamide (co)polymers via aRAFT: Toward a cell penetrating peptide mimic," ACS Macro Letters, 2012, 1:100-104.
Wang et al., "Localization of bioadhesive precursors of the sandcastle worm, Phragmatopoma californica (Fewkes)," J. Exp. Biol., 2012, 215:351-361.
Berg et al., "The thermal transition of a non-hydroxylated form of collagen: eviidence for a role for hydroxyproline in stabilizing the triple-helix of collagen," Biochem. Biophys. Res. Commun., 1973, 52:115-120.
Hwang et al., "Expression of functional recombinant mussel adhesive protein Mgfp-5 in *Escherichia coli*," Applied and Environmental Microbiology, 2004, 70:3352-3359.
Johnston et al., "The effect of comb architecture on complex coacarvation," Organic and Biomolecular Chemistry, 2017, 841:14pp.
Kamachi et al., "Synthesis of block polymers for desalination membranes: preparation of block copolymers of 2-vinylpyridine and methacrylic acid or acrylic acid," Macromolecules, 1972, 5:161-168.
Kayitmazer et al., "Mesophase separation and probe dynamics in protein-polyelectrolyte coacervates," Chemical Engineering Faculty Publications, 2007, 3:1064-1076.
Lee et al., "Rapid gel formation and adhesion in photocurable and biodegradable block copolymers with high DOPA content," Macromolecules, 2006, 39:1740-1748.
Lee et al., "Single-molecule meachanics of mussel adhesion," Proc. Natl. Acad. Sci. USA, 2006, 103:12999-13003.
Lee et al., "Synthesis of 3,4-dihydroxyphenylalanine (DOPA) containing monomers and their co-polymerization with PEG-diacrylate to form hydrogels," J. Biomater. Sci. Polymer Edn., 2004, 15:449-464.
Lim et al., "The adhesive properties of coacervated recombinant hybrid mussel," Blomaterials, 2010, 31:3715-3722.
Liu et al., "Chemistry of periodate mediated cross-linking of 3,4-dihydroxylphenylalanine-containg molecules to proteins," J. Am. Chem. Soc., 2008, 128:15228-15235.
Mo et al., "Soft tissue adhesive composed of modified gelatin and polysaccharides," J. Biomater. Sci. Polymer Edn., 2000, 11:341-351.
"Polyethyleneimine:EPOMIN," <https://www.shokubai.co.jp/en/products/functionality/epomin1.html> Accessed Feb. 16, 2015, 2pp.
Shao et al., "A water-borne adhesive modeled after the sandcastle glue of P. californica," Macromolecular Bioscience, 2008, 9:464-471.

(56) References Cited

OTHER PUBLICATIONS

Stevens et al., "Multiscale structure of the underwater adhesive of Phragmatopoma californica: a nanostructured latex with a sleep microporosity gradient," Langmuir, 2007, 23:5045-5040.

Stewart et al., "The lube cement of Phragmatopoma calfornica: a solid foam," J. Experimental Biol., 2004, 207:4727-4734.

Wang et al., "A novel bioadhesive protein of silk filaments spun underwater by caddisfly larvae," Adv. Mater. Res., 2009, 79-82:1631-1634.

Yu et al., "Synthetic polypeptide mimics of marine adhesives," Macromolecules, 1998, 31:4739-4745.

Zhao et al., "Cement proteins of the tube-building Phragmatopoma californica," J. Biol. Chem., 2005, 280:42938-42944.

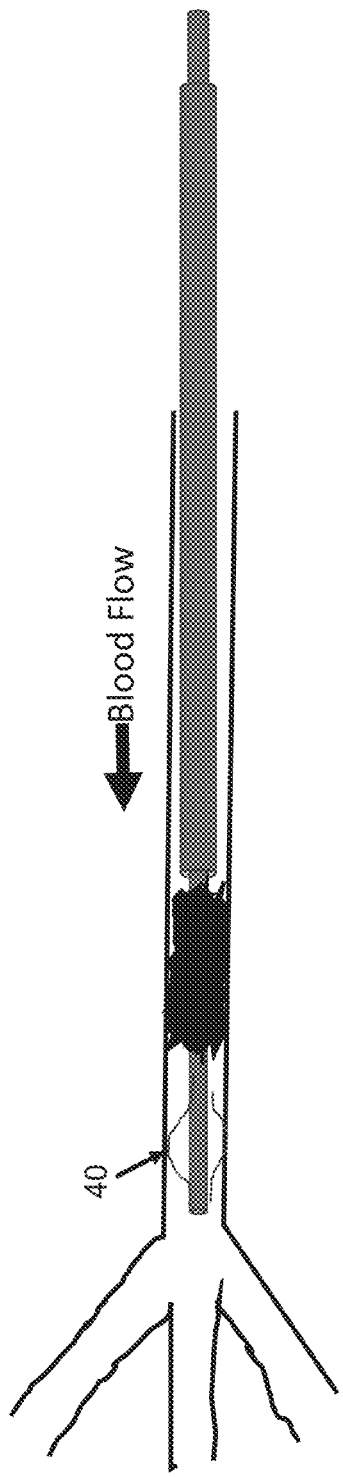

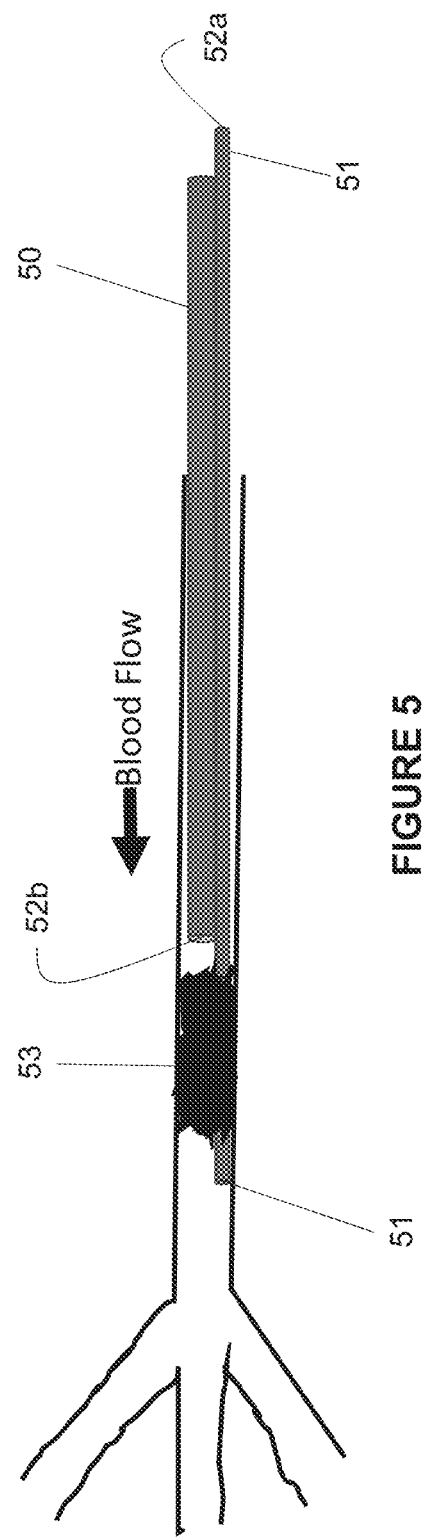

APPARATUS AND METHOD OF USING IN SITU SOLIDIFYING COMPLEX COACERVATES FOR VASCULAR OCCLUSION

CROSS REFERENCE TO RELATED APPLICATIONS

This application claims priority upon U.S. provisional application Ser. No. 62/622,195, filed Jan. 26, 2018. This application is hereby incorporated by reference in its entirety.

CROSS REFERENCE TO SEQUENCE LISTING

Proteins described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Potential clinical applications of in situ gelling systems include transarterial and transvenous embolization procedures. Transarterial embolization is a procedure in which a microcatheter is inserted by a clinician into an artery then guided to the target therapeutic area to then deliver the embolic agent to selectively block blood flow typically distal to the delivered embolic agent. Transarterial embolization is used to treat abnormal vasculature such as, for example, devascularize tumors including but not limited to the liver, kidney, head, neck, colon; occlude aneurysms, occlude endoleaks between stent grafts and native vasculature; embolized arteriovenous malformations; occlude distal microvascular bleeding including but not limited to gastrointestinal bleeding; therapeutically occlude or slow blood flow feeding fibroids; occlude or slow flow into the prostate for treatment of benign prostatic hyperplasia (BPH) and erectile dysfunction; and other like uses.

Current embolic agents have serious drawbacks. Cyanoacrylate (CA) adhesives are used in some cases as embolization agents. The cyanoacrylate monomers rapidly polymerized into a hard resin when they contact water in the blood vessel. CA is difficult to control as it polymerizes rapidly and can glue the end of the catheter to the blood vessels making catheter removal difficult. CA also does not allow a clinician to inject, let the CA set up, and then allow the clinician to use the catheter tip to dotter or compact the recently injected CA into the vessel without risk of the newly injected CA sticking to the catheter tip. Onyx® is an injectable dimethylsulfoxide (DMSO) solution of ethylenevinyl alcohol. When it is injected into a watery physiological environment, the DMSO solvent diffuses out of the material causing the ethylenevinyl alcohol, which is insoluble in water, to precipitate. A drawback of Onyx® is that it can be used only in small amounts because of the toxicity of the DMSO solvent. The injection rate of Onyx® is limited and, therefore can make it difficult to control forward flow and distal penetration. DMSO typically clumps during injection reducing the predictability of solidification and targeting control. DMSO has other delivery issues similar to CA.

Other embolic agents, such as particles, are prone to unpredictable delivery and control resulting in less than optimal vessel targeting. Particles also flow distal and completely fill the vasculature distal to the catheter reducing or eliminating the clinician's ability to create a plug where the embolic seals the vessel for a discrete length with blood held in stasis with no embolic distal to the plug. Liquid embolics provide better distal penetration but have risks of potentially gluing the catheter in place or at the embolization site.

Targeted, and focused, delivery of drugs, fluids, and other materials to precise locations within the vasculature is a clinical challenge. Blood flow may carry agents downstream away from the intended target vessel and/or area resulting in a lower amount of drug, or material, being injected into the target. In addition, any material that is released into a vessel and flows downstream away from the target may result in unintended consequences in the healthy, non-targeted, areas of the body.

SUMMARY

Described herein are the use of fluid complex coacervates that produce solid adhesives in situ to anchor medical devices such as catheters in a blood vessel. The anchored devices permit the targeted delivery of bioactive agents. The anchored devices can perform as an embolic agent by reducing or preventing blood flow in the vessel. Additionally, the embolic produced from the solid adhesive produced in situ can also include one or more bioactive agents that can be released in a controlled manner.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 3-6 shows the use in situ solidifying complex coacervates to anchor single and dual catheters in a blood vessel.

DETAILED DESCRIPTION

Figure 1:
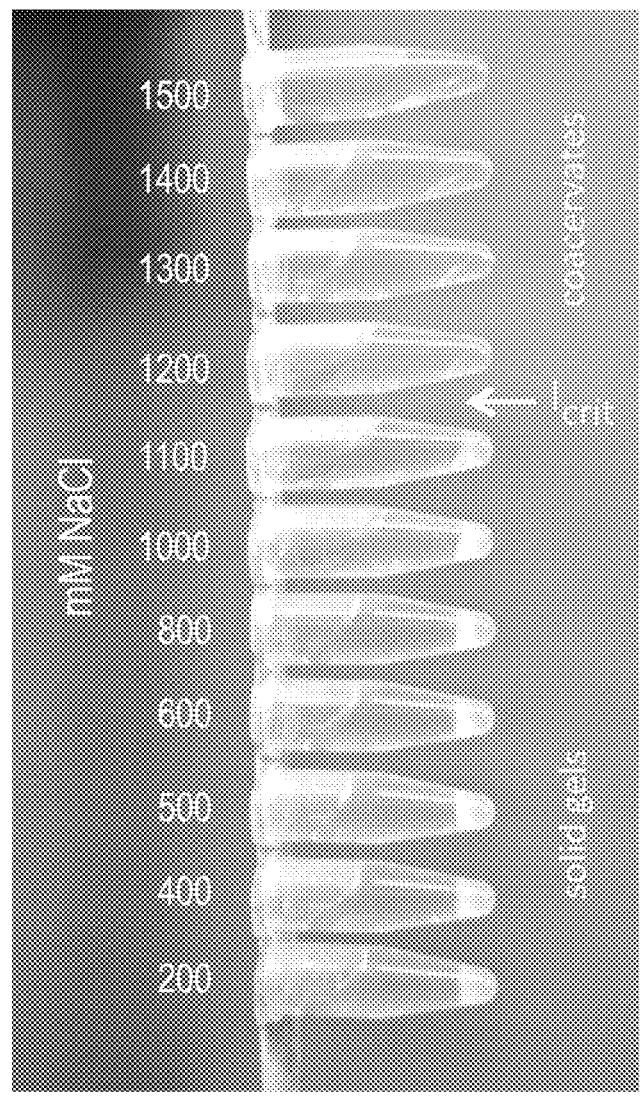
FIG. 1 shows aqueous solutions of protamine and hexametaphosphate mixed in various concentrations of NaCl. Between 1100 and 1200 mM NaCl a critical ionic strength (I) exists at which the complex coacervate becomes a solid non-flowing gel. The viscosity of the coacervate decreases with increasing I above $I_{crit}$. The stiffness of the gels increases below $I_{crit}$. The forms are interconvertible by changing the ionic strength.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed.

Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, a palmitate group. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aryl group" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. In one aspect, the heteroaryl group is imidazole. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "nucleophilic group" includes any groups capable of reacting with an activated ester. Examples include amino groups, thiols groups, hydroxyl groups, and their corresponding anions.

The term "carboxyl group" includes a carboxylic acid and the corresponding salt thereof.

The term "amino group" as used herein is represented as the formula —NHRR', where R and R' can be any organic group including alkyl, aryl, carbonyl, heterocycloalkyl, and the like, where R and R' can be separate groups or be part of a ring. For example, pyridine is a heteroaryl group where R and R' are part of the aromatic ring.

The term "treat" as used herein is defined as maintaining or reducing the symptoms of a pre-existing condition. The term "prevent" as used herein is defined as eliminating or reducing the likelihood of the occurrence of one or more symptoms of a disease or disorder. The term "reduce" as used herein is the ability of the in situ solidifying complex coacervate described herein to completely eliminate the activity or reduce the activity when compared to the same activity in the absence of the complex coacervate.

"Subject" refers to mammals including, but not limited to, humans, non-human primates, sheep, dogs, rodents (e.g., mouse, rat, etc.), guinea pigs, cats, rabbits, cows, and non-mammals including chickens, amphibians, and reptiles.

"Physiological conditions" refers to condition such as pH, temperature, etc. within the subject. For example, the physiological pH and temperature of a human is 7.2 and 37° C., respectively.

In Situ Solidifying Complex Coacervates

Polyelectrolytes with opposite net charges in aqueous solution can associate into several higher order morphologies depending on the solution conditions and charge ratios. They can form stable colloidal suspensions of polyelectrolyte complexes with net surface charges. Repulsion between like surface charges stabilize the suspension from further association. When the polyelectrolyte charge ratios are balanced, or near balance, the initial complexes can further coalesce and settle out into a dense fluid phase in which the opposite macroion charges are approximately equal. This process is referred to as complex coacervation, and the dense fluid morphology as a complex coacervate. More descriptively, the process is an associative macrophase separation of an aqueous solution of two oppositely charged polyelectrolytes into two liquid phases, a dense concentrated polyelectrolyte phase in equilibrium with a polyelectrolyte depleted phase. The aqueous coacervate phase can be dispersed into the aqueous depleted phase but quickly settles back out, like oil droplets in water. The spontaneous demixing of paired polyelectrolytes into complex coacervates occurs when attractive forces between polyelectrolyte pairs are stronger than repulsive forces. In thermodynamic terms, the net negative change in free energy that drives complex coacervation derives primarily from the gain in entropy of the small counterions released when macroions associate, which overcomes the loss of configurational entropy of the fully solvated polyelectrolytes.

Figures 2A, 2B:
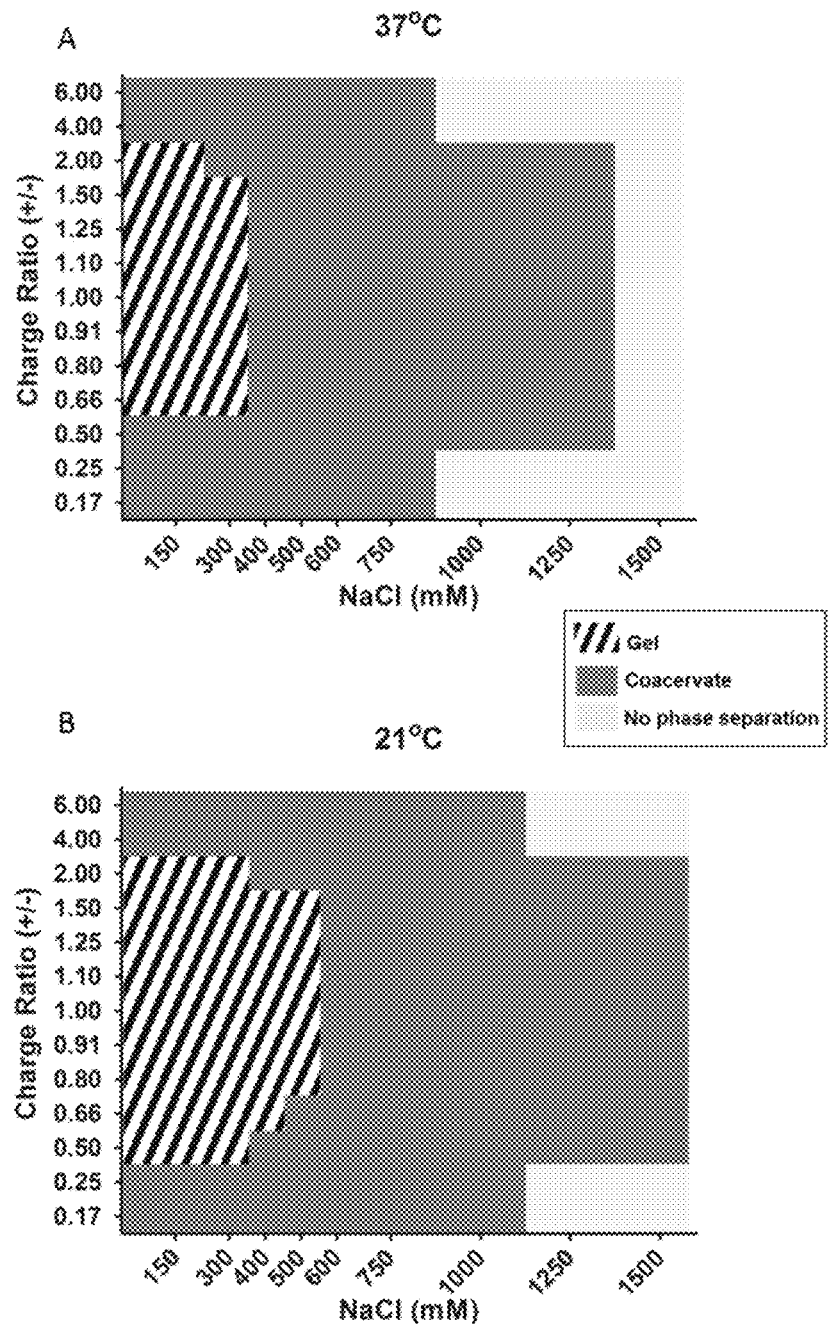
FIG. 2A shows the phase diagram of PRT/IP6 polyelectrolyte mixtures over a range of NaCl concentrations at 37° C.
FIG. 2B shows the phase diagram of PRT/IP6 polyelectrolyte mixtures over a range of NaCl concentrations at 21° C.

A non-limiting example of the different morphologies that can be produced from polyelectrolytes with opposite net charges is provided in FIGS. 1 and 2. As shown in the phase diagrams in FIGS. 2A and 2B, varying parameters such as charge ratio of the polyelectrolytes, temperature, salt concentration, and pH can result in the formation of a gel, a complex coacervate, or a clear homogeneous solution, i.e., no phase separation (FIG. 1). By mixing polyelectrolytes in a region of the phase diagram in which fluid complex coacervates form, the in situ solidifying complex coacervates described herein can be prepared in a fluid form. If the fluid form is introduced into an environment corresponding to a gel region of the phase diagram (FIG. 2), the fluid form will harden into a solid gel as the in situ solidifying complex coacervate equilibrates to the new solution conditions. The term "gel" is defined herein as non-fluid colloidal network or polymer network that is expanded throughout its whole volume by a fluid. IUPAC. Compendium of Chemical Terminology, 2nd ed. (the "Gold Book"). Compiled by A. D. McNaught and A. Wilkinson. Blackwell Scientific Publications, Oxford (1997). Conversely, the fluid complex coacervates described herein are liquids. Thus, the fluid complex coacervates described herein have a completely different morphology compared to corresponding gels produced in situ despite the fact that the polycation and polyanion in the fluid complex coacervate and the gel are identical.

The following aspects are described herein and will be discussed in greater detail below.

Anchored Catheters and Applications Thereof

As discussed above, the in situ solidifying complex coacervates are fluids with low viscosity and are readily injectable. The in situ solidifying complex coacervates are water-borne eliminating the need for potentially toxic solvents such as, for example, DMSO.

The in situ solidifying complex coacervates described herein are fluids at ionic strengths higher than the ionic strength of the application site, but insoluble ionic hydrogels at the ionic strength when introduced into a blood vessel of a subject. When the fluid, high ionic strength complex coacervates are introduced into a lower ionic strength application site, the complex coacervate forms a solid or gel (i.e., embolus) in situ in the blood vessel as the salt concentration in the complex coacervate equilibrates to the salt concentration in the vessel. The solid or gel that is subsequently produced is a non-fluid, water insoluble material in the vessel that acts as an adhesive. The adhesive can function as an embolus to partially or completely block the flow of blood through the vessel.

The in situ solidifying complex coacervates can form solids or gels in situ under physiological conditions. The physiological ionic strength is approximately 300 mOsm/L. Thus, when in situ solidifying complex coacervates having an ionic strength greater than 300 mOsm/L are introduced into a blood vessel of a subject, the fluid complex coacervate is converted to an adhesive solid or gel at the site of application. In one aspect, the blood present in the vessel has one or more monovalent salts, where the concentration of the monovalent salts is less than 500 mM, or from 150 mM to less than 500 mM. In another aspect, the ionic concentration of the monovalent salt in the blood is from 150 mM to 600 mM and the concentration of the monovalent salt of the complex coacervate composition is greater than 600 mM to 2 M.

The ability of the fluid complex coacervates described herein to be converted to an adhesive solid or gel permits the anchoring of medical devices within the vessel. In one embodiment, a catheter can be anchored to the inner wall of a blood vessel. In another aspect, two catheters can be inserted into a blood vessel and subsequently anchored to the inner wall of the vessel using the in situ solidifying complex coacervates. In this aspect, the catheter can be anchored in the vessel and be used as a delivery device for one or more bioactive agents for an extended period of time.

FIGS. 3-6 depict several embodiments for using the in situ solidifying complex coacervates to anchor a catheter in a blood vessel. In one aspect, a first catheter and a second catheter can be inserted into a blood vessel of a subject, wherein the second catheter is extended further into the vessel (distal) than the first catheter (proximal).

Figure 3:
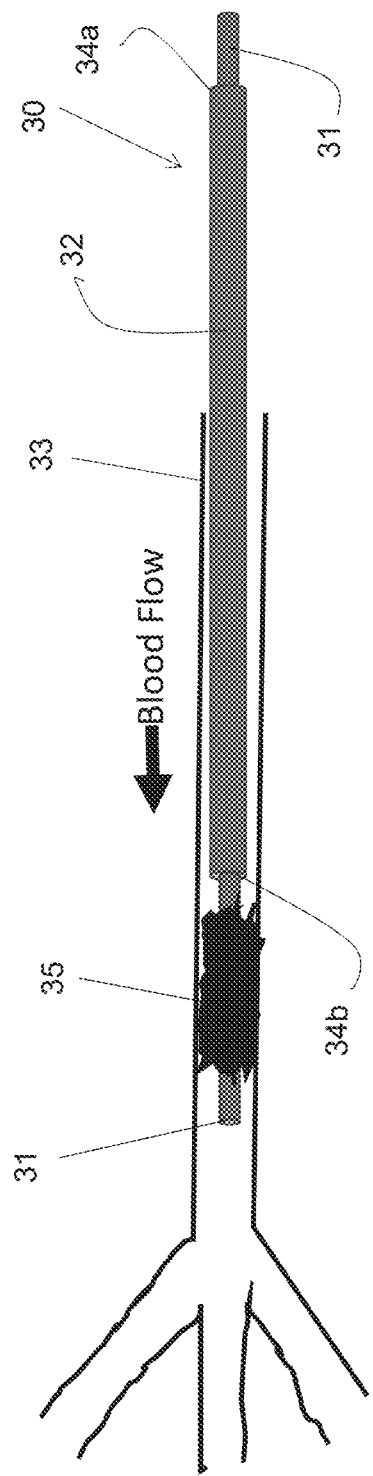

In one aspect, the first catheter and second catheter are part of a co-axial catheter. This feature is depicted in FIG. 3 as co-axial catheter 30, where the second catheter 31 is inserted in the first catheter 32. The co-axial catheter 30 is inserted into vessel 33 and positioned accordingly. Once in the vessel, the second catheter 31 can be extended from the first catheter 32. At this point, the in situ solidifying complex coacervate is injected into the first catheter 32 only via aperture 34a. When the fluid complex coacervate exits the aperture 34b of the first catheter, a solid embolus or plug 35 is formed. Additionally, the embolus or plug adheres the second catheter 31 to the inner wall of the vessel. The first catheter 32 can be removed, and the second catheter 31 remains anchored in the vessel. A variation of the embodiment in FIG. 3 is depicted in FIG. 4. In this embodiment, the second catheter is an occlusion balloon catheter 40. Once anchored in the vessel, one or more bioactive agents can be injected into the second catheter 31 and delivered to the targeted area.

Another aspect of a two catheter system is depicted in FIG. 5. In this embodiment, the first catheter 50 and second catheter 51 are sistered to one another. In one aspect, the first and second catheter are not physically attached to one another so that the first catheter can be removed from the vessel once the second catheter has been anchored to the vessel. As shown in FIG. 5, the second catheter 51 is extended further into the vessel relative to the first catheter 50. At this point, the in situ solidifying complex coacervate is injected into the first catheter 50 via aperture 52a. When the fluid complex coacervate exits the aperture 52b of the first catheter, a solid embolus or plug 53 is formed. Additionally, the embolus or plug adheres the second catheter 51 to the inner wall of the vessel. The first catheter 50 can be removed, and the second catheter 51 remains anchored in the vessel. Once anchored in the vessel, one or more bioactive agents can be injected into the second catheter 51 and delivered to the targeted area.

Figure 6A:
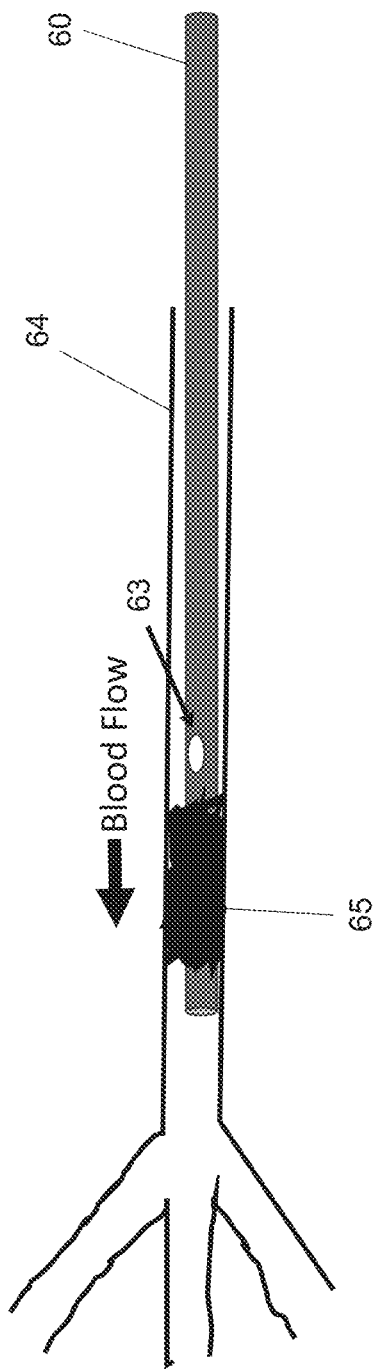
Figure 6B:
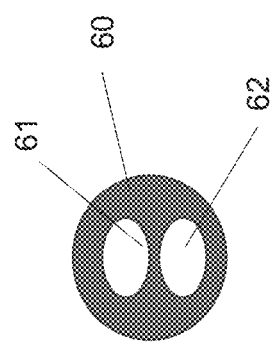

In other aspects, a single catheter can be anchored within the blood vessel. An example of this embodiment is depicted in FIGS. 6A and 6B. Referring to FIGS. 6A and 6B, the catheter 60 has a first lumen 61 and a second lumen 62. The catheter 60 also has an outer aperture 63 accessing the first lumen 61. The catheter 60 is inserted into vessel 64 and positioned accordingly. At this point, the in situ solidifying complex coacervate is injected into the catheter 60 into the first lumen 61. When the fluid complex coacervate exits the aperture 63 of catheter 60, a solid embolus or plug 65 is formed. Additionally, the embolus or plug adheres the catheter 60 to the inner wall of the vessel. Once anchored in the vessel, one or more bioactive agents can be injected into the second lumen 62 and delivered to the targeted area.

In any of the embodiments described above, the catheter can be removed from the embolus and the vessel. The resulting hole in the embolus can subsequently be filled with additional in situ solidifying complex coacervate to enclose the hole and preserve the embolus.

The use of the in situ solidifying complex coacervates to anchor delivery devices such as catheters within a blood vessel provides options and many potential benefits for the clinician. Targeted and focused delivery of bioactive agents and other materials to precise locations within the vasculature is a clinical challenge. Blood flow may carry agents downstream away from the intended target vessel and/or area resulting in a lower amount of bioactive agent or material, being injected into the target. In addition, any material that is released into a vessel and flows downstream away from the target may result in unintended consequences in the healthy, non-targeted, areas of the body.

The specific and controlled delivery of a bioactive agent or other materials can be delivered directly into the targeted area through the anchored catheter. Targeted infusion may increase the effectiveness of the bioactive agent where loss of bioactive agent due to flow in the vasculature system can be minimized. Furthermore, the catheter that is anchored in the vessel can act as a portal for the delivery of other materials and/or devices to a specific target vessel and/or area.

The bioactive agent that can be administered to a subject using the methods described herein can be any drug including, but not limited to, antibiotics, pain relievers, immune modulators, growth factors, enzyme inhibitors, hormones, mediators, messenger molecules, cell signaling molecules, receptor agonists, oncolytics, chemotherapy agents, receptor antagonists, diagnostic media, radioactive isotopes, other fluids (gas to liquid). The agent may also be autologous or homologous (allogeneic) cells, platelet rich plasma (PRP), or other like tissue.

In another aspect, the bioactive agent can be a nucleic acid. The nucleic acid can be an oligonucleotide, deoxyribonucleic acid (DNA), ribonucleic acid (RNA), or peptide nucleic acid (PNA). The nucleic acid of interest can be nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In another aspect, the bioactive agent can be an anti-angiogenic agent. Anti-angiogenic agents are in general hydrophobic molecules, and the in situ solidifying liquid complex coacervates permit the delivery of these molecules in aqueous environments. In one aspect, the coacervates disclosed herein are effective vehicles for the delivery of high local concentrations of anti-angiogenic agents.

In one aspect, the anti-angiogenic agent is present in an amount of from 0.1 mg/mL to 100 mg/mL of in situ solidifying liquid complex coacervate. Further in this aspect, the anti-angiogenic agent is present at about 0.1, 0.25, 0.5, 0.75, 1, 1.5, 2, 2.5, 3, 3.5, 4, 4.5, 5, 10, 15, 20, 25, 30, 35, 40, 45, 50, 55, 60, 65, 70, 75, 80, 85, 90, 95, or 100 mg/mL of in situ solidifying liquid complex coacervate, where any value can be a lower and upper end-point of a range (e.g., 0.1 to 10 mg/mL, etc.).

In one aspect, the anti-angiogenic agent is an FDA-approved anti-angiogenic agent. In one aspect, the anti-angiogenic agent is a tyrosine kinase inhibitor (TKI). Not wishing to be bound by theory, angiogenesis is, in large part, initiated and maintained by cell signaling through receptor tyrosine kinases (RTKs). In one aspect, RTKs include receptors for several angiogenesis promoters, including VEGF, which stimulates vascular permeability, proliferation, and migration of endothelial cells; PDGF, which recruits pericytes and smooth muscle cells that support the budding endothelium; and FGF, which stimulates proliferation of endothelial cells, smooth muscle cells, and fibroblasts.

In one aspect, the anti-angiogenic agent is a TKI such as sunitinib malate (SUN), pazopanib hydrochloride (PAZ), sorafenib tosylate (SOR), vandetanib (VAN), cabozantinib, or any combination thereof.

In one aspect, inclusion of an anti-angiogenic agent such as a TKI does not affect the material properties or setting reaction of the in situ solidifying liquid complex coacervate. In another aspect, the effective plasma concentration of a TKI when administered orally is as low as 50 ng/mL. Further in this aspect, the coacervates described herein allow for delivery of high concentrations of TKIs directly into hypervascular tumors while simultaneously cutting off blood supply to the tumors.

In an alternative aspect, humanized anti-VEGF and anti-VEGFR Fab' fragments can be incorporated into the in situ solidifying liquid complex coacervates. In this aspect, electrostatic interactions can control release kinetics. In one aspect, the native charge of the Fab' fragment is sufficient to interact with the polyelectrolyte components of the coacervate. In another aspect, the native charge of the Fab' fragment is insufficient to interact with the polyelectrolyte components of the coacervate and the Fab' fragment is modified to increase charge density by attaching a short polyelectrolyte to reactive sulfhydryl groups using maleamide conjugation chemistries.

In one aspect, the anti-angiogenic agent is an anti-VEGF antibody. In a still further aspect, the anti-VEGF antibody is bevacizumab or is a biosimilar anti-VEGF antibody, or is an anti-VEGF antibody derivative such as, for example, ranibizumab.

In one aspect, the anchored catheter can be used to reduce or inhibit blood flow in a blood vessel of a subject. The in situ solidifying liquid complex coacervates form a seal around the catheter, where the catheter and solid adhesive together act as an embolic agent to prevent blood flow through the vessel. The use of the anchored catheter as an embolic has numerous applications including hemostasis or the creation of an artificial embolism to inhibit blood flow to a tumor, aneurysm, varicose vein, an arteriovenous malformation, or other vascular defects.

In another aspect, the in situ solidifying liquid complex coacervates can include one or more bioactive agents. Thus, in one aspect, the embolus that is formed around the catheter can deliver a bioactive agent in a sustained manner. Thus, in one aspect, a first bioactive agent can be administered through the anchored catheter while a second bioactive agent can be released over time from the embolus. In this aspect, the first and second bioactive agent can be the same or different agents. Any of the bioactive agents described herein can be used in this application.

In another aspect, the coacervates include a water-soluble chemotherapeutic agent such as, for example, doxorubicin. In one aspect, the chemotherapeutic agent is present in an amount of from 0.001 mg/mL to 100 mg/mL of in situ solidifying liquid complex coacervate. Further in this aspect, the anti-angiogenic agent is present at about 0.001, 0.05, 0.1, 0.25, 0.5, 0.75, 1, 1.5, 2, 2.5, 3, 3.5, 4, 4.5, 5, 10, 15, 20, 25, 30, 35, 40, 45, 50, 55, 60, 65, 70, 75, 80, 85, 90, 95, or 100 mg/mL of in situ solidifying liquid complex coacervate, where any value can be a lower and upper end-point of a range (e.g., 0.1 to 10 mg/mL, etc.).

In another aspect, the in situ solidifying liquid complex coacervates described herein can include one or more bioactive agents in combination with an anti-inflammatory agent in order to reduce or prevent inflammation at the site where the complex coacervate is administered to the subject. In one aspect the anti-inflammatory agent is an NSAIDs including, but are not limited to, acetaminophen, aspirin, ibuprofen, naproxen sodium, naproxen, indomethacin, flurbiprofen, ketoprofen, lornoxicam, meloxicam, piroxicam, oxaprozin, etodolac, ketorolac, nabumetone, or other non-selective nonsteroidal anti-inflammatory drugs (NSAIDs).

In anotyer aspect the anti-inflammatory agent is a COX-2 inhibitors including, but not limited to, celecoxib, rofecoxib, valdecoxib, parecoxib, etoricoxib, CS-502, JTE-522, L-745, 337, and NS398). In another aspect the anti-inflammatory agent is corticosteroid including, but not limited to, cortisol, cortisone, prednisone, prednisolone, methylprednisolone, dexamethasone, betamethasone, triamcinolone, fludrocortisones acetate, and deoxycorticosterone acetate.

The components used to produce the in situ solidifying complex coacervates described herein as well as their applications thereof are provided below. The components disclosed in international published application no. WO 2016/011028, which is incorporated by reference in its entirety, can be used to produce the in situ solidifying complex coacervates described herein.

I. Polycations

The polycation is generally composed of a polymer backbone with a plurality of cationic groups at a particular pH. The cationic groups can be pendant to the polymer backbone and/or incorporated within the polymer backbone. In certain aspects, (e.g., biomedical applications), the polycation is any biocompatible polymer possessing cationic groups or groups that can be readily converted to cationic groups by adjusting the pH. In one aspect, the polycation is a polyamine compound. The amino groups of the polyamine can be branched or part of the polymer backbone. The amino group can be a primary, secondary, or tertiary amino group that can be protonated to produce a cationic ammonium group at a selected pH. In general, the polyamine is a polymer with a large excess of positive charges relative to negative charges at the relevant pH, as reflected in its isoelectric point (pI), which is the pH at which the polymer has a net neutral charge. The number of amino groups present on the polycation ultimately determines the charge density of the polycation at a particular pH. For example, the polycation can have from 10 to 90 mole %, 10 to 80 mole %, 10 to 70 mole %, 10 to 60 mole %, 10 to 50 mole %, 10 to 40 mole %, 10 to 30 mole %, or 10 to 20 mole % amino groups. In one aspect, the polyamine has excess positive charges at a pH of about 7, with a pI significantly greater than 7. As will be discussed below, additional amino groups can be incorporated into the polymer in order to increase the pI value.

In one aspect, the amino group can be derived from a residue of lysine, histidine, or arginine attached to the polycation. For example, arginine has a guanidinyl group, where the guanidinyl group is a suitable amino group useful herein. Any anionic counterions can be used in association with the cationic polymers. The counterions should be physically and chemically compatible with the essential components of the composition and do not otherwise unduly impair product performance, stability or aesthetics. Non-limiting examples of such counterions include halides (e.g., chloride, fluoride, bromide, iodide), sulfate, methylsulfate, acetate and other monovalent carboxylic acids.

In one aspect, the polycation can be a positively-charged protein produced from a natural organism. For example, a recombinant *P. californica* protein can be used as the polycation. In one aspect, Pc1, Pc2, Pc4-Pc18 (SEQ ID NOS 1-17) can be used as the polycation. The type and number of amino acids present in the protein can vary in order to achieve the desired solution properties. For example, Pc1 is enriched with lysine (13.5 mole %) while Pc4 and Pc5 are enriched with histidine (12.6 and 11.3 mole %, respectively).

In another aspect, the polycation is a recombinant protein produced by artificial expression of a gene or a modified gene or a composite gene containing parts from several genes in a heterologous host such as, for example, bacteria, yeast, cows, goats, tobacco, and the like.

In another aspect, the polycation can be a biodegradable polyamine. The biodegradable polyamine can be a synthetic polymer or naturally-occurring polymer. The mechanism by which the polyamine can degrade will vary depending upon the polyamine that is used. In the case of natural polymers, they are biodegradable because there are enzymes that can hydrolyze the polymer chain. For example, proteases can hydrolyze natural proteins like gelatin. In the case of synthetic biodegradable polyamines, they also possess chemically labile bonds. For example, β-aminoesters have hydrolyzable ester groups. In addition to the nature of the polyamine, other considerations such as the molecular weight of the polyamine and crosslink density of the adhesive can be varied in order to modify the rate of biodegradability.

In one aspect, the biodegradable polyamine includes a polysaccharide, a protein, or a synthetic polyamine. Polysaccharides bearing one or more amino groups can be used herein. In one aspect, the polysaccharide is a natural polysaccharide such as chitosan or chemically modified chitosan. Similarly, the protein can be a synthetic or naturally-occurring compound. In another aspect, the biodegradable polyamine is a synthetic polyamine such as poly(β-aminoesters), polyester amines, poly(disulfide amines), mixed poly(ester and amide amines), and peptide crosslinked polyamines.

In the case when the polycation is a synthetic polymer, a variety of different polymers can be used; however, in certain applications such as, for example, biomedical applications, it is desirable that the polymer be biocompatible and non-toxic to cells and tissue. In one aspect, the biodegradable polyamine can be an amine-modified natural polymer. For example, the amine-modified natural polymer can be gelatin modified with one or more alkylamino groups, heteroaryl groups, or an aromatic group substituted with one or more amino groups. Examples of alkylamino groups are depicted in Formulae IV-VI

IV

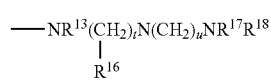

V

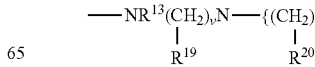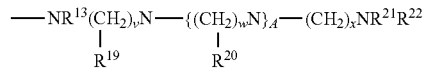

VI wherein $R^{13}$-$R^{22}$ are, independently, hydrogen, an alkyl group, or a nitrogen containing substituent;

s, t, u, v, w, and x are an integer from 1 to 10; and

A is an integer from 1 to 50, where the alkylamino group is covalently attached to the natural polymer. In one aspect, if the natural polymer has a carboxyl group (e.g., acid or ester), the carboxyl group can be reacted with an alkyldiamino compound to produce an amide bond and incorporate the alkylamino group into the polymer. Thus, referring to formulae IV-VI, the amino group $NR^{13}$ is covalently attached to the carbonyl group of the natural polymer.

As shown in formula IV-VI, the number of amino groups can vary. In one aspect, the alkylamino group is —$NHCH_2NH_2$, —$NHCH_2CH_2NH_2$, —$NHCH_2CH_2CH_2NH_2$, —$NHCH_2CH_2CH_2CH_2NH_2$, —$NHCH_2CH_2CH_2CH_2CH_2NH_2$, —$NHCH_2NHCH_2CH_2CH_2NH_2$, —$NHCH_2CH_2NHCH_2CH_2CH_2NH_2$, —$NHCH_2CH_2CH_2NHCH_2CH_2CH_2NHCH_2CH_2CH_2NH_2$, —$NHCH_2CH_2NHCH_2CH_2CH_2CH_2NH_2$, —$NHCH_2CH_2NHCH_2CH_2CH_2NHCH_2CH_2CH_2NH_2$, or —$NHCH_2CH_2NH(CH_2CH_2NH)_dCH_2CH_2NH_2$, where d is from 0 to 50.

In one aspect, the amine-modified natural polymer can include an aryl group having one or more amino groups directly or indirectly attached to the aromatic group. Alternatively, the amino group can be incorporated in the aromatic ring. For example, the aromatic amino group is a pyrrole, an isopyrrole, a pyrazole, imidazole, a triazole, or an indole. In another aspect, the aromatic amino group includes the isoimidazole group present in histidine. In another aspect, the biodegradable polyamine can be gelatin modified with ethylenediamine.

In another aspect, the polycation can be a polycationic micelle or mixed micelle formed with cationic surfactants. The cationic surfactant can be mixed with nonionic surfactants to create micelles with variable charge densities. The micelles are polycationic by virtue of the hydrophobic interactions that form a polyvalent micelle. In one aspect, the micelles have a plurality of amino groups capable of reacting with the activated ester groups present on the polyanion.

Examples of nonionic surfactants include the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij™ surfactants from ICI. Tergitol™ 15-S Surfactants include $C_{11}$-$C_{15}$ secondary alcohol polyethylenegly col ethers. Brij™97 surfactant is polyoxyethylene(10) oleyl ether; Brij™58 surfactant is polyoxyethylene (20) cetyl ether; and Brij™ 76 surfactant is polyoxyethylene (10) stearyl ether.

Another useful class of nonionic surfactants include the polyethylene oxide condensates of one mole of alkyl phenol containing from about 6 to 12 carbon atoms in a straight or branched chain configuration, with ethylene oxide. Examples of nonreactive nonionic surfactants are the Igepal™ CO and CA series from Rhone-Poulenc. Igepal™CO surfactants include nonylphenoxy poly(ethyleneoxy)ethanols. Igepal™ CA surfactants include octylphenoxy poly(ethyleneoxy)ethanols.

Another useful class of hydrocarbon nonionic surfactants include block copolymers of ethylene oxide and propylene oxide or butylene oxide. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers.

In other aspects, the nonionic surfactants include sorbitan fatty acid esters, polyoxyethylene sorbitan fatty acid esters and polyoxyethylene stearates. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{15}$ sorbitan monoesters. Myj™ surfactants include poly(ethylene oxide) stearates.

In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Examples of cationic surfactants useful for making cationic micelles include alkylamine salts and quaternary ammonium salts. Non-limiting examples of cationic surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022, 844; and amino surfactants as discussed in U.S. Pat. No. 6,221,825 and WO 00/47708, specifically amido propyldimethyl amine (APA).

In one aspect, the polycation includes a polyacrylate having one or more pendant amino groups. For example, the backbone of the polycation can be derived from the polymerization of acrylate monomers including, but not limited to, acrylates, methacrylates, acrylamides, and the like. In one aspect, the polycation backbone is derived from polyacrylamide. In other aspects, the polycation is a block co-polymer, where segments or portions of the co-polymer possess cationic groups or neutral groups depending upon the selection of the monomers used to produce the co-polymer.

In other aspects, the polycation can be a dendrimer. The dendrimer can be a branched polymer, a multi-armed polymer, a star polymer, and the like. In one aspect, the dendrimer is a polyalkylimine dendrimer, a mixed amino/ether dendrimer, a mixed amino/amide dendrimer, or an amino acid dendrimer. In another aspect, the dendrimer is poly (amidoamine), or PAMAM. In one aspect, the dendrimer has 3 to 20 arms, wherein each arm comprises an amino group.

In one aspect, the polycation is a polyamino compound. In another aspect, the polyamino compound has 10 to 90 mole % primary amino groups. In a further aspect, the polycation polymer has at least one fragment of the formula I

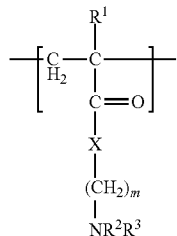

I wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof. In another aspect, $R^1$, $R^2$, and $R^3$ are methyl and m is 2. Referring to formula I, the polymer backbone is composed of $CH_2$—$CR^1$ units with pendant —$C(O)X(CH_2)_m NR^2 R^3$ units. In one aspect, the polycation is the free radical polymerization product of a cationic primary amine monomer (3-aminopropyl methacrylate) and acrylamide, where the molecular weight is from 10 to 200 kd and possesses primary monomer concentrations from 5 to 90 mol %.

In another aspect, the polycation is a protamine. Protamines are polycationic, arginine-rich proteins that play a role in condensation of chromatin into the sperm head during spermatogenesis. As by-products of the fishing industry, commercially available protamines, purified from fish sperm, are readily available in large quantity and are relatively inexpensive. A non-limiting example of a protamine useful herein is salmine. The amino acid sequence of salmine, a protamine isolated from salmon sperm, is SEQ ID NO 18. Of the 32 amino acids, 21 are arginine (R). The guanidinyl group on the sidechain of R has a $pK_a$ of ~12.5, making salmine a densely charged polycation at physiologically relevant pH. It has a molecular mass of ~4,500 g/mol and a single negative charge at the carboxy terminus. In another aspect, the protamine is clupein.

In one aspect, the protamine can be derivatized with one or more crosslinkable groups described herein. For example, salmine can be derivatized to include one or more acrylate or methacrylate groups. In this aspect, salmine has been derivatized on the C-terminal carboxylate with a single methacrylamide group to create a crosslinkable polycation.

In one aspect, the polycation is a natural polymer wherein one or more amine present on the natural polymer has been modified with a guanidine group. In another aspect, the polycation is a synthetic polymer containing one or more guanidinyl sidechains. For example, the polycation can be a synthetic polyguanidinyl polymer having an acrylate or methacrylate backbone and one or more guanidinyl sidechains. In another aspect, the polycation polymer has at least one fragment of the formula XX

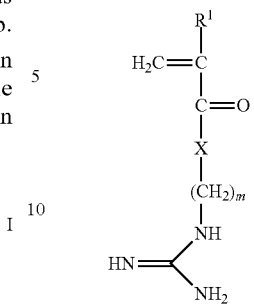

XX wherein $R^1$ is a hydrogen or an alkyl group, X is oxygen or $NR^5$, where $R^5$ is a hydrogen or an alkyl group, and m is from 1 to 10, or the pharmaceutically acceptable salt thereof. In one aspect, in the compound of formula I, $R^1$ is methyl, X is NH, and m is 3. In another aspect, the monomer is methacrylamide.

In a further aspect, the mole ratio of the guanidinyl monomer of formula I to the monomer is from 1:1 to 10:1, or is 1:1, 2:1, 3:1, 4:1, 5:1, 6:1, 7:1, 8:1, 9:1, or 10:1, where any ratio can be a lower and upper end-point of a range (e.g., 2:1 to 5:1, etc.). In one aspect, the mole ratio of the guanidinyl monomer of formula I to the monomer is from 3:1 to 4:1.

The polyguanidinyl copolymer can be synthesized by using polymerization techniques known in the literature such as, for example, RAFT polymerization (i.e., reversible addition-fragmentation chain-transfer polymerization) or other methods such as free radical polymerization. In a further aspect, the polymerization reaction can be carried out in an aqueous environment.

In one aspect, the molecular weight distribution of the polyguanidinyl copolymer is distributed around an average molecular weight between 5 kDa to 100 kDa, or can be about 5, 10, 15, 20, 25, 30, 35, 40, 45, 50, 55, 60, 65, 70, 75, 80, 85, 90, 95, or 100 kDa, where any value can be a lower and upper end-point of a range (e.g., 10 to 30 kDa, etc.).

In another aspect, multiple copolymers with controlled $M_m$ and narrow polydispersity indices (PDIs) can be synthesized by RAFT polymerization. In one aspect, the copolymer has an average molar weight ($M_m$) from about 2 kg/mol to about 80 kg/mol, or can be about 2, 3, 4, 5, 10, 15, 20, 25, 30, 35, 40, 45, 50, 55, 60, 65, 70, 75, or 80 kg/mol, where any value can be a lower and upper end-point of a range (e.g., 10 to 25 kg/mol, etc.).

In another aspect, the polyguanidinyl copolymer is a multimodal polyguanidinyl copolymer. The term "multimodal polyguanidinyl copolymer" is polyguanidinyl copolymer with a distribution curve being the sum of at least two or more molecular weight unimodal distribution curves. In one aspect, the polyguanidinyl copolymer has a multimodal distribution of polyguanidinyl copolymer molecular weights with modes between 5 and 100 kDa, or can be about 5, 10, 15, 20, 25, 30, 35, 40, 45, 50, 55, 60, 65, 70, 75, 80, 85, 90, 95, or 100 kDa, where any value can be a lower and upper end-point of a range (e.g., 10 to 30 kDa, etc.).

In another aspect, the number of guanidinyl side groups can vary from about 50 to about 100 mol %, or can be about 50, 55, 60, 65, 70, 75, 80, 85, 90, 95, or 100 mol %, where any value can be a lower and upper end-point of a range (e.g., 60 to 90 mol %, etc.). In one aspect, the guanidinyl side groups are from about 70 to about 80 mol % of the polyguanidinyl copolymer. Conversely, comonomer concentration can vary from about 50 to about 0 mol %, or can be about 50, 45, 40, 35, 30, 25, 20, 15, 10, 5, or 0 mol %, where any value can be a lower and upper end-point of a range (e.g., 10 to 40 mol %, etc.). In one aspect, the $M_n$, PDI, and structures of the copolymers can be verified by size exclusion chromatography (SEC), $^1$H NMR, and $^{13}$C NMR or other common techniques. Exemplary procedures for preparing and characterizing co polymers useful herein are provided in the Examples below.

II. Polyanions

Similar to the polycation, the polyanion can be a synthetic polymer or naturally-occurring. Examples of naturally-occurring polyanions include glycosaminoglycans such as condroitin sulfate, heparin, heparin sulfate, dermatan sulfate, keratin sulfate, and hyaluronic acid. In other aspects, acidic proteins having a net negative charge at neutral pH or proteins with a low pI can be used as naturally-occurring polyanions described herein. The anionic groups can be pendant to the polymer backbone and/or incorporated in the polymer backbone.

When the polyanion is a synthetic polymer, it is generally any polymer possessing anionic groups or groups that can be readily converted to anionic groups by adjusting the pH. Examples of groups that can be converted to anionic groups include, but are not limited to, carboxylate, sulfonate, boronate, sulfate, borate, phosphonate, or phosphate. Any cationic counterions can be used in association with the anionic polymers if the considerations discussed above are met.

In one aspect, the polyanion is a polyphosphate. In another aspect, the polyanion is a polyphosphate compound having from 5 to 90 mole % phosphate groups. For example, the polyphosphate can be a naturally-occurring compound such as, for example, DNA, RNA, or highly phosphorylated proteins like phosvitin (an egg protein), dentin (a natural tooth phosphoprotein), casein (a phosphorylated milk protein), or bone proteins (e.g. osteopontin).

Alternatively, the polyphosphoserine can be a synthetic polypeptide made by polymerizing the amino acid serine and then chemically phosphorylating the polypeptide. In another aspect, the polyphosphoserine can be produced by the polymerization of phosphoserine. In one aspect, the polyphosphate can be produced by chemically or enzymatically phosphorylating a protein (e.g., natural serine- or threonine-rich proteins). In a further aspect, the polyphosphate can be produced by chemically phosphorylating a polyalcohol including, but not limited to, polysaccharides such as cellulose or dextran.

In another aspect, the polyphosphate can be a synthetic compound. For example, the polyphosphate can be a polymer with pendant phosphate groups attached to the polymer backbone and/or present in the polymer backbone. (e.g., a phosphodiester backbone).

In another aspect, the polyanion can be a micelle or mixed micelle formed with anionic surfactants. The anionic surfactant can be mixed with any of the nonionic surfactants described above to create micelles with variable charge densitites. The micelles are polyanionic by virtue of the hydrophobic interactions that form a polyvalent micelle.

Other useful anionic surfactants include, but are not limited to, alkali metal and (alkyl)ammonium salts of 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8)N-acyltaurine derivatives such as sodium N methyl-N-oleyltaurate); 9) amine oxides including alkyl and alkylamidoalkyldialkylamine oxides; and 10) alkyl phosphate mono or di-esters such as ethoxylated dodecyl alcohol phosphate ester, sodium salt.

Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL™ A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the tradename AEROSOL™ OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and or dodecylbenzenesulfonic acid sold under BIO-SOFT® AS-100 from Stepan Chemical Co. In one aspect, the surfactant can be a disodium alpha olefin sulfonate, which contains a mixture of $C_{12}$ to $C_{16}$ sulfonates. In one aspect, CALSOFT™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates.

Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340KL from Clariant Corp., as well as PPG-5 cetyl 10 phosphate available under the trade designation CRODAPHOS™ SG from Croda Inc., Parsipanny, N.J.

Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In one aspect, the polyanion includes a polyacrylate having one or more pendant phosphate groups. For example, the polyanion can be derived from the polymerization of acrylate monomers including, but not limited to, acrylates, methacrylates, and the like. In other aspects, the polyanion is a block co-polymer, where segments or portions of the co-polymer possess anionic groups and neutral groups depending upon the selection of the monomers used to produce the co-polymer.

In one aspect, the polyanion includes two or more carboxylate, sulfate, sulfonate, borate, boronate, phosphonate, or phosphate groups.

In another aspect, the polyanion is a polymer having at least one fragment having the formula XI

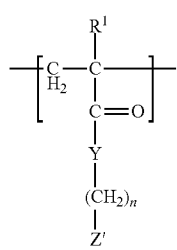

XI wherein $R^4$ is hydrogen or an alkyl group;
n is from 1 to 10;
Y is oxygen, sulfur, or $NR^{30}$, wherein $R^{30}$ is hydrogen, an alkyl group, or an aryl group;
Z' is an anionic group or a group that can be converted to an anionic group, or the pharmaceutically-acceptable salt thereof.

In one aspect, Z' in formula XI is carboxylate, sulfate, sulfonate, borate, boronate, a substituted or unsubstituted phosphate, or a phosphonate. In another aspect, Z' in formula XI is sulfate, sulfonate, borate, boronate, a substituted or unsubstituted phosphate, or a phosphonate, and n in formulae XI is 2.

In one aspect, the polyanion is an inorganic polyphosphate possessing a plurality of phosphate groups (e.g., $NaPO_3)_n$, where n is 3 to 10 or is 3, 4, 5, 6, 7, 8, 9, or 10). Examples of inorganic phosphate include, but are not limited to, Graham salts, hexametaphosphate salts, and triphosphate salts. The counterions of these salts can be monovalent cations such as, for example, $Na^+$, $K^+$, $NH_4^+$, or a combination thereof. In one aspect, the polyanion is sodium hexametaphosphate.

In another aspect, the polyanion is a phosphorylated sugar. The sugar can be a hexose or pentose sugar. Additionally, the sugar can be partially or fully phosphorylated. In one aspect, the phosphorylated sugar is inositol hexaphosphate (IP6).

III. Salts that Produce Ions

Any salt that produces an ion in water can be used in the complex coacervates described herein. The concentration and identity of the salt can be varied depending upon the application and conditions (e.g., pH, valency of the salt, etc.) of which the in situ liquid complex coacervate is used.

In one aspect, the salt is a monovalent salt. The monovalent salt can be any salt that produces monovalent ions in water. In one aspect, the monovalent salt can be a biocompatible salt such as, for example, sodium chloride, sodium acetate, sodium carbonate, or any combination thereof.

In another aspect, the salt produces zwitterions in water. For example, the salt can produce a zwitterion by varying the pH of the solution. In one aspect, an amino acid salt can produce zwitterions in the complex coacervates described herein.

In another aspect, the compound can be a multivalent salt that produces ions having a plus or minus charge of greater than or equal to 2. In one aspect, the multivalent salt can be a salt of a compound possessing two or more carboxylic acid groups (e.g., a tartrate salt, a citrate salt, etc.). In another aspect the multivalent salt can be a phosphate salt (e.g., sodium phosphate).

In another aspect, the salt that produces ions is present at a concentration of from 1.5 to 10 times greater than the concentration of the ions at the administration site of the subject. The concentration of the ions present in the subject can vary in the subject; thus, the concentration of the salt that produces ions in the complex coacervate can be tailored to specific applications. In one aspect, the salt concentration in the complex coacervate is 1.5, 2, 2.5, 3, 3.4, 4, 4.5, 5, 5.5, 6, 6.5, 7, 7.5, 8, 8.5, 9, 9.5, or 10 times greater than the concentration of the ions at the administration site of the subject, where any value can be a lower and upper end-point of a range (e.g., 2.5 to 7.5, etc.). In another aspect, the salt concentration can be from about 150 to about 1500 mM, or can be about 150, 200, 250, 300, 350, 400, 450, 500, 550, 600, 650, 700, 750, 800, 850, 900, 950, 1000, 1100, 1150, 1200, 1250, 1300, 1400, or 1500 mM, where any value can be a lower and upper end-point of a range (e.g., 1,000 to 1,400 mM, etc.). In one aspect, the salt is NaCl and the concentration is about 1200 mM (1.2 M).

In one aspect, the in situ solidifying liquid complex coacervate can be formulated in hypertonic saline solutions that can be used for parenteral or intravenous administration or by injection to a subject. In one aspect, the in situ solidifying liquid complex coacervate can be formulated in Ringer's dextrose, dextrose and sodium chloride, lactated Ringer's, or other buffered saline solutions that can be safely administered to a subject, wherein the saline concentration has been adjusted so that it is greater than saline concentration at physiological conditions.

IV. Bioactive Agents

The in situ solidifying complex coacervates described herein can include one or more bioactive agents. The bioactive agents can be any drug including, but not limited to, antibiotics, pain relievers, immune modulators, growth factors, enzyme inhibitors, hormones, mediators, messenger molecules, cell signaling molecules, receptor agonists, oncolytics, chemotherapy agents, receptor antagonists, diagnostic media, radioactive isotopes, other fluids (gas to liquid). The agent may also be autologous or homologous (allogeneic) cells, platelet rich plasma (PRP), or other like tissue.

In another aspect, the bioactive agent can be a nucleic acid. The nucleic acid can be an oligonucleotide, deoxyribonucleic acid (DNA), ribonucleic acid (RNA), or peptide nucleic acid (PNA). The nucleic acid of interest can be nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In another aspect, the bioactive agent can be an antiangiogenic agent. Anti-angiogenic agents are in general hydrophobic molecules, and the in situ solidifying liquid complex coacervates permit the delivery of these molecules in aqueous environments. In one aspect, the coacervates disclosed herein are effective vehicles for the delivery of high local concentrations of anti-angiogenic agents.

In one aspect, the anti-angiogenic agent is present in an amount of from 0.1 mg/mL to 100 mg/mL of in situ solidifying liquid complex coacervate. Further in this aspect, the anti-angiogenic agent is present at about 0.1, 0.25, 0.5, 0.75, 1, 1.5, 2, 2.5, 3, 3.5, 4, 4.5, 5, 10, 15, 20, 25, 30, 35, 40, 45, 50, 55, 60, 65, 70, 75, 80, 85, 90, 95, or 100 mg/mL of in situ solidifying liquid complex coacervate, where any value can be a lower and upper end-point of a range (e.g., 0.1 to 10 mg/mL, etc.).

In one aspect, the anti-angiogenic agent is an FDA-approved anti-angiogenic agent. In one aspect, the anti-angiogenic agent is a tyrosine kinase inhibitor (TKI). Not wishing to be bound by theory, angiogenesis is, in large part, initiated and maintained by cell signaling through receptor tyrosine kinases (RTKs). In one aspect, RTKs include receptors for several angiogenesis promoters, including VEGF, which stimulates vascular permeability, proliferation, and migration of endothelial cells; PDGF, which recruits pericytes and smooth muscle cells that support the budding endothelium; and FGF, which stimulates proliferation of endothelial cells, smooth muscle cells, and fibroblasts.

In one aspect, the anti-angiogenic agent is a TKI such as sunitinib malate (SUN), pazopanib hydrochloride (PAZ), sorafenib tosylate (SOR), vandetanib (VAN), cabozantinib, or any combination thereof.

In one aspect, inclusion of an anti-angiogenic agent such as a TKI does not affect the material properties or setting reaction of the in situ solidifying liquid complex coacervate. In another aspect, the effective plasma concentration of a TKI when administered orally is as low as 50 ng/mL. Further in this aspect, the coacervates described herein allow for delivery of high concentrations of TKIs directly into hypervascular tumors while simultaneously cutting off blood supply to the tumors.

In an alternative aspect, humanized anti-VEGF and anti-VEGFR Fab' fragments can be incorporated into the in situ solidifying liquid complex coacervates. In this aspect, electrostatic interactions can control release kinetics. In one aspect, the native charge of the Fab' fragment is sufficient to interact with the polyelectrolyte components of the coacervate. In another aspect, the native charge of the Fab' fragment is insufficient to interact with the polyelectrolyte components of the coacervate and the Fab' fragment is modified to increase charge density by attaching a short polyelectrolyte to reactive sulfhydryl groups using maleamide conjugation chemistries.

In one aspect, the anti-angiogenic agent is an anti-VEGF antibody. In a still further aspect, the anti-VEGF antibody is bevacizumab or is a biosimilar anti-VEGF antibody, or is an anti-VEGF antibody derivative such as, for example, ranibizumab.

V. Contrast Agents

In one aspect, the in situ solidifying liquid complex coacervates disclosed herein are formulated with a contrast agent. In a further aspect, the contrast agent is a radiographic contrast agent. Further in this aspect, the radiographic contrast agent can be tantalum metal particles (Ta), gold particles, or an iodide salt (e.g., sodium iodide). In one aspect, up to 30% (w/w) of Ta can be included in the formulations. In one aspect, inclusion of Ta can be beneficial to interventional radiologists in the operating room. In another aspect, the contrast agent can be a fluoroscopic contrast agent. Further in this aspect, the fluoroscopic contrast agent can be tantalum oxide ($TaO_2$, $Ta_2O_5$) particles. In one aspect, the contrast agent can be tantalum particles having a particle size from 0.5 μm to 50 μm, 1 μm to 25 μm, 1 μm to 10 μm, or 1 μm to 5 μm. In another aspect, contrast agent is tantalum particles in the amount of 10% to 60%, 20% to 50%, or 20% to 40%.

VI. Crosslinkable Groups

In certain aspects, the polycations and polyanions can contain groups that permit crosslinking between the two polymers upon curing to produce new covalent bonds. The mechanism of crosslinking can vary depending upon the selection of the crosslinking groups. In one aspect, the crosslinking groups can be electrophiles and nucleophiles. For example, the polyanion can have one or more electrophilic groups, and the polycations can have one or more nucleophilic groups capable of reacting with the electrophilic groups to produce new covalent bonds. Examples of electrophilic groups include, but are not limited to, anhydride groups, esters, ketones, lactams (e.g., maleimides and succinimides), lactones, epoxide groups, isocyanate groups, and aldehydes. Examples of nucleophilic groups are presented below. In one aspect, the polycation and polyanion can crosslink with one another via a Michael addition. For example, the polycation can have one or more nucleophilic groups such as, for example, a hydroxyl or thiol group that can react with an olefinic group present on the polyanion.

In one aspect, the crosslinking group on the polyanion comprises an olefinic group and the crosslinking group on the polycation comprises a nucleophilic group that reacts with the olefinic group to produce a new covalent bond. In another aspect, the crosslinking group on the polycation comprises an olefinic group and the crosslinking group on the polyanion comprises a nucleophilic group that reacts with the olefinic group to produce a new covalent bond.

In another aspect, the polycation and polyanion each have an actinically crosslinkable group. As used herein, "actinically crosslinkable group" in reference to curing or polymerizing means that the crosslinking between the polycation and polyanion is performed by actinic irradiation, such as, for example, UV irradiation, visible light irradiation, ionizing radiation (e.g. gamma ray or X-ray irradiation), microwave irradiation, and the like. Actinic curing methods are well-known to a person skilled in the art. The actinically crosslinkable group can be an unsaturated organic group such as, for example, an olefinic group. Examples of olefinic groups useful herein include, but are not limited to, an acrylate group, a methacrylate group, an acrylamide group, a methacrylamide group, an allyl group, a vinyl group, a vinylester group, or a styrenyl group. In another aspect, the actinically crosslinkable group can be an azido group. For example, crosslinking can occur between the polycation and polyanion via light activated crosslinking through azido groups.

Any of the polymers described above (synthetic or naturally-occurring) that can be used as the polycation and polyanion can be modified to include the actinically crosslinkable group.

In another aspect, the crosslinkable group includes a dihydroxy-substituted aromatic group capable of undergoing oxidation in the presence of an oxidant. In one aspect, the dihydroxy-substituted aromatic group is an ortho-dihydroxy aromatic group capable of being oxidized to the corresponding quinone. In another aspect, the dihydroxyl-substituted aromatic group is a dihydroxyphenol or halogenated dihydroxyphenol group such as, for example, DOPA and catechol (3,4 dihydroxyphenol). For example, in the case of DOPA, it can be oxidized to dopaquinone. Dopaquinone is capable of either reacting with a neighboring DOPA group or another nucleophilic group. In the presence of an oxidant such as oxygen or other additives including, but not limited to, peroxides, periodates (e.g., $NaIO_4$), persulfates, permanganates, dichromates, transition metal oxidants (e.g., a $Fe^{+3}$ compound, osmium tetroxide), or enzymes (e.g., catechol oxidase), the dihydroxyl-substituted aromatic group can be oxidized.

In one aspect, the polyanion is the polymerization product between two or more monomers, where one of the monomers has a dihydroxy aromatic group covalently attached to the monomer. For example, the polyanion can be the polymerization product between (1) a phosphate acrylate and/or phosphate methacrylate and (2) a second acrylate and/or second methacrylate having a dihydroxy aromatic group covalently bonded to the second acrylate or second methacrylate. In another aspect, the polyanion is the polymerization product between methacryloxyethyl phosphate and dopamine methacrylamide. In each of these polymers, an acrylate containing the pendant ortho-dihydroxyphenyl residue is polymerized with the appropriate monomers to produce the polyanion with pendant ortho-dihydroxyphenyl residues. Oxidation of ortho-dihydroxyphenyl groups results in orthoquinone groups, a reactive intermediate and can crosslink (i.e., react) with nucleophiles such as, for example, amino, hydroxyl, or thiol groups via a Michael-type addition to form a new covalent bond. For example, a lysyl group on the polycation can react with the orthoquinone residue on the polyanion to produce new covalent bonds. Other groups such as, for example, tyrosine or alkyl phenol groups can be used herein. Alkyl phenol groups can be crosslinked with peroxidase enzymes, e.g. horse radish peroxidase in the presence of $H_2O_2$. The importance of crosslinking with respect to the use of the adhesive complex coacervates described herein will be discussed below.

In certain aspects, the oxidant used above can be stabilized. For example, a compound that forms a complex with periodate that is not redox active can result in a stabilized oxidant. In other words, the periodate is stabilized in a non-oxidative form and cannot oxidize the ortho-dihydroxy-substituted aromatic group while in the complex. The complex is reversible and even if it has a very high stability constant there is a small amount of uncomplexed periodate formed. The ortho-dihydroxyl-substituted aromatic group competes with the compound for the small amount of free periodate. As the free periodate is oxidized more is released from the equilibrium complex. In one aspect, sugars possessing a cis,cis-1,2,3-triol grouping on a six-membered ring can form competitive periodate complexes. An example of a specific compound that forms stable periodate complex is 1,2-O-isopropylidene-alpha-D-glucofuranose (A. S. Perlin and E. VON Rudloff, Canadian Journal of Chemistry. Volume 43 (1965)). The stabilized oxidant can control the rate of crosslinking. Not wishing to be bound by theory, the stabilized oxidant slows the rate of oxidation providing time to add the oxidant and position the substrate before the adhesive hardens irreversibly.

In other aspects, the crosslinkers present on the polycation and/or polyanion can form coordination complexes with transition metal ions. In one aspect, the polycation and/or polyanion can include groups capable of coordinating transition metal ions. Examples of coordinating sidechains are catechols, imidazoles, phosphates, carboxylic acids, and combinations. The rate of coordination and dissociation can be controlled by the selection of the coordination group, the transition metal ion, and the pH. Thus, in addition to covalent crosslinking as described above, crosslinking can occur through electrostatic, ionic, coordinative, or other non-covalent bonding. Transition metal ions such as, for example, iron, copper, vanadium, zinc, and nickel can be used herein. In one aspect, the transition metal is present in an aqueous environment at the application site.

In certain aspects, the in situ solidifying complex coacervate can also include a multivalent crosslinker. In one aspect, the multivalent crosslinker has two or more nucleophilic groups (e.g., hydroxyl, thiol, etc.) that react with crosslinkable groups (e.g., olefinic groups) present on the polycation and polyanion via a Michael addition reaction to produce a new covalent bond. In one aspect, the multivalent crosslinker is a di-thiol or tri-thiol compound.

VII. Reinforcing Components

The in situ solidifying complex coacervates described herein can optionally include a reinforcing component. The term "reinforcing component" is defined herein as any component that enhances or modifies one or more properties of the fluid complex coacervates described herein (e.g., cohesiveness, fracture toughness, elastic modulus, dimensional stability after curing, viscosity, etc.) of the in situ solidifying complex coacervate prior to or after the curing of the coacervate when compared to the same coacervate that does not include the reinforcing component. The mode in which the reinforcing component can enhance the mechanical properties of the coacervate can vary, and will depend upon the intended application of the coacervates as well as the selection of the polycation, polyanion, and reinforcing component. For example, upon curing the coacervate, the polycations and/or polyanions present in the coacervate can covalently crosslink with the reinforcing component. In other aspects, the reinforcing component can occupy a space or "phase" in the coacervate, which ultimately increases the mechanical properties of the coacervate. Examples of reinforcing components useful herein are provided below.

In one aspect, the reinforcing component is a polymerizable monomer. The polymerizable monomer entrapped in the complex coacervate can be any water soluble monomer capable of undergoing polymerization in order to produce an interpenetrating polymer network. In certain aspects, the interpenetrating network can possess nucleophilic groups (e.g., amino groups) that can react (i.e., crosslink) with the activated ester groups present on the polyanion. The selection of the polymerizable monomer can vary depending upon the application. Factors such as molecular weight can be altered to modify the solubility properties of the polymerizable monomer in water as well as the mechanical properties of the resulting coacervate, The selection of the functional group on the polymerizable monomer determines the mode of polymerization. For example, the polymerizable monomer can be a polymerizable olefinic monomer that can undergo polymerization through mechanisms such as, for example, free radical polymerization and Michael addition reactions. In one aspect, the polymerizable monomer has two or more olefinic groups. In one aspect, the monomer comprises one or two actinically crosslinkable groups as defined above.

Examples of water-soluble polymerizable monomers include, but are not limited to, hydroxyalkyl methacrylate (HEMA), hydroxyalkyl acrylate, N-vinyl pyrrolidone, N-methyl-3-methylidene-pyrrolidone, allyl alcohol, N-vinyl alkylamide, N-vinyl-N-alkylamide, acrylamides, methacrylamide, (lower alkyl)acrylamides and methacrylamides, and hydroxyl-substituted (lower alkyl)acrylamides and -methacrylamides. In one aspect, the polymerizable monomer is a diacrylate compound or dimethacrylate compound. In another aspect, the polymerizable monomer is a polyalkylene oxide glycol diacrylate or dimethacrylate. For example, the polyalkylene can be a polymer of ethylene glycol, propylene glycol, or block copolymers thereof. In one aspect, the polymerizable monomer is polyethylene glycol diacrylate or polyethylene glycol dimethacrylate. In one aspect, the polyethylene glycol diacrylate or polyethylene glycol dimethacrylate has a $M_n$ of 200 to 2,000, 400 to 1,500, 500 to 1,000, 500 to 750, or 500 to 600.

In certain aspects, the interpenetrating polymer network is biodegradable and biocompatible for medical applications. Thus, the polymerizable monomer is selected such that a biodegradable and biocompatible interpenetrating polymer network is produced upon polymerization. For example, the polymerizable monomer can possess cleavable ester linkages. In one aspect, the polymerizable monomer is hydroxypropyl methacrylate (HPMA), which will produce a biocompatible interpenetrating network. In other aspects, biodegradable crosslinkers can be used to polymerize biocompatible water soluble monomers such as, for example, alkyl methacrylamides. The crosslinker could be enzymatically degradable, like a peptide, or chemically degradable by having an ester or disulfide linkage. In another aspect, the reinforcing component can be a natural or synthetic fiber.

In other aspects, the reinforcing component can be a water-insoluble filler. The filler can have a variety of different sizes and shapes, ranging from particles (micro and nano) to fibrous materials. The selection of the filler can vary depending upon the application of the in situ solidifying complex coacervate.

The fillers useful herein can be composed of organic and/or inorganic materials. In one aspect, the nanostructures can be composed of organic materials like carbon or inorganic materials including, but not limited to, boron, molybdenum, tungsten, silicon, titanium, copper, bismuth, tungsten carbide, aluminum oxide, titanium dioxide, molybdenum disulphide, silicon carbide, titanium diboride, boron nitride, dysprosium oxide, iron (III) oxide-hydroxide, iron oxide, manganese oxide, titanium dioxide, boron carbide, aluminum nitride, or any combination thereof.

In certain aspects, the fillers can be functionalized in order to react (i.e., crosslink) with the polycation and/or polyanion. For example, the filler can be functionalized with amino groups or activated ester groups. In other aspects, it is desirable to use two or more different types of fillers. For example, a carbon nanostructure can be used in combination with one or more inorganic nanostructures.

In one aspect, the filler comprises a metal oxide, a ceramic particle, or a water insoluble inorganic salt. Examples of fillers useful herein include those manufactured by Sky-Spring Nanomaterials, Inc., which is listed below.

Metals and Non-Metal Elements
Ag, 99.95%, 100 nm
Ag, 99.95%, 20-30 nm
Ag, 99.95%, 20-30 nm, PVP coated
Ag, 99.9%, 50-60 nm
Ag, 99.99%, 30-50 nm, oleic acid coated
Ag, 99.99%, 15 nm, 10 wt %, self-dispersible
Ag, 99.99%, 15 nm, 25 wt %, self-dispersible
Al, 99.9%, 18 nm
Al, 99.9%, 40-60 nm
Al, 99.9%, 60-80 nm
Al, 99.9%, 40-60 nm, low oxygen
Au, 99.9%, 100 nm
Au, 99.99%, 15 nm, 10 wt %, self-dispersible
B, 99.9999%
B, 99.999%
B, 99.99%
B, 99.9%
B, 99.9%, 80 nm
Diamond, 95%, 3-4 nm
Diamond, 93%, 3-4 nm
Diamond, 55-75%, 4-15 nm
Graphite, 93%, 3-4 nm
Super Activated Carbon, 100 nm
Co, 99.8%, 25-30 nm
Cr, 99.9%, 60-80 nm
Cu, 99.5%, 300 nm
Cu, 99.5%, 500 nm
Cu, 99.9%, 25 nm
Cu, 99.9%, 40-60 nm
Cu, 99.9%, 60-80 nm
Cu, 5-7 nm, dispersion, oil soluble
Fe, 99.9%, 20 nm
Fe, 99.9%, 40-60 nm
Fe, 99.9%, 60-80 nm
Carbonyl-Fe, micro-sized
Mo, 99.9%, 60-80 nm
Mo, 99.9%, 0.5-0.8 m
Ni, 99.9%, 500 nm (adjustable)
Ni, 99.9%, 20 nm
Ni coated with carbon, 99.9%, 20 nm
Ni, 99.9%, 40-60 nm
Ni, 99.9%, 60-80 nm
Carbonyl-Ni, 2-3 m
Carbonyl-Ni, 4-7 m
Carbonyl-Ni—Al (Ni Shell, Al Core)
Carbonyl-Ni—Fe Alloy
Pt, 99.95%, 5 nm, 10 wt %, self-dispersible
Si, Cubic, 99%, 50 nm
Si, Polycrystalline, 99.99995%, lumps
Sn, 99.9%, <100 nm
Ta, 99.9%, 60-80 nm
Ti, 99.9%, 40-60 nm
Ti, 99.9%, 60-80 nm
W, 99.9%, 40-60 nm
W, 99.9%, 80-100 nm
Zn, 99.9%, 40-60 nm
Zn, 99.9%, 80-100 nm
Metal Oxides
AlOOH, 10-20 nm, 99.99%
$Al_2O_3$ alpha, 98+%, 40 nm
$Al_2O_3$ alpha, 99.999%, 0.5-10 m
$Al_2O_3$ alpha, 99.99%, 50 nm
$Al_2O_3$ alpha, 99.99%, 0.3-0.8 m
$Al_2O_3$ alpha, 99.99%, 0.8-1.5 m
$Al_2O_3$ alpha, 99.99%, 1.5-3.5 m
$Al_2O_3$ alpha, 99.99%, 3.5-15 m
$Al_2O_3$ gamma, 99.9%, 5 nm
$Al_2O_3$ gamma, 99.99%, 20 nm
$Al_2O_3$ gamma, 99.99%, 0.4-1.5 m
$Al_2O_3$ gamma, 99.99%, 3-10 m
$Al_2O_3$ gamma, Extrudate
$Al_2O_3$ gamma, Extrudate
$Al(OH)_3$, 99.99%, 30-100 nm
$Al(OH)_3$, 99.99%, 2-10 m
Aluminium Iso-Propoxide (AIP), $C_9H_{21}O_3Al$, 99.9%
AlN, 99%, 40 nm
$BaTiO_3$, 99.9%, 100 nm
$BBr_3$, 99.9%
$B_2O_3$, 99.5%, 80 nm
BN, 99.99%, 3-4 m
BN, 99.9%, 3-4 m
$B_4C$, 99%, 50 nm
$Bi_2O_3$, 99.9%, <200 nm
$CaCO_3$, 97.5%, 15-40 nm
$CaCO_3$, 15-40 nm
$Ca_3(PO_4)_2$, 20-40 nm
$Ca_{10}(PO_4)_6(OH)_2$, 98.5%, 40 nm
$CeO_2$, 99.9%, 10-30 nm CoO, <100 nm
$Co_2O_3$, <100 nm
$Co_3O_4$, 50 nm
CuO, 99+%, 40 nm
$Er_2O_3$, 99.9%, 40-50 nm
$Fe_2O_3$ alpha, 99%, 20-40 nm
$Fe_2O_3$ gamma, 99%, 20-40 nm
$Fe_3O_4$, 98+%, 20-30 nm
$Fe_3O_4$, 98+%, 10-20 nm
$Gd_2O_3$, 99.9%<100 nm
$HfO_2$, 99.9%, 100 nm
$In_2O_3:SnO_2$=90:10, 20-70 nm
$In_2O_3$, 99.99%, 20-70 nm
$In(OH)_3$, 99.99%, 20-70 nm
$LaB_6$, 99.0%, 50-80 nm
$La_2O_3$, 99.99%, 100 nm
$LiFePO_4$, 40 nm
MgO, 99.9%, 10-30 nm
MgO, 99%, 20 nm
MgO, 99.9%, 10-30 nm
$Mg(OH)_2$, 99.8%, 50 nm
$Mn_2O_3$, 98+%, 40-60 nm
$MoCl_5$, 99.0%
$Nd_2O_3$, 99.9%, <100 nm
NiO, <100 nm
$Ni_2O_3$, <100 nm
$Sb_2O_3$, 99.9%, 150 nm
$SiO_2$, 99.9%, 20-60 nm
$SiO_2$, 99%, 10-30 nm, treated with Silane Coupling Agents
$SiO_2$, 99%, 10-30 nm, treated with Hexamethyldisilazane
$SiO_2$, 99%, 10-30 nm, treated with Titanium Ester
$SiO_2$, 99%, 10-30 nm, treated with Silanes
$SiO_2$, 10-20 nm, modified with amino group, dispersible
$SiO_2$, 10-20 nm, modified with epoxy group, dispersible
$SiO_2$, 10-20 nm, modified with double bond, dispersible
$SiO_2$, 10-20 nm, surface modified with double layer, dispersible
$SiO_2$, 10-20 nm, surface modified, super-hydrophobic & oleophilic, dispersible
$SiO_2$, 99.8%, 5-15 nm, surface modified, hydrophobic & oleophilic, dispersible
$SiO_2$, 99.8%, 10-25 nm, surface modified, super-hydrophobic, dispersible
SiC, beta, 99%, 40 nm
SiC, beta, whisker, 99.9%
$Si_3N_4$, amorphous, 99%, 20 nm
$Si_3N_4$ alpha, 97.5-99%, fiber, 100 nm×800 nm
$SnO_2$, 99.9%, 50-70 nm
ATO, $SnO_2:Sb_2O_3$=90:10, 40 nm
$TiO_2$ anatase, 99.5%, 5-10 nm
$TiO_2$ Rutile, 99.5%, 10-30 nm
$TiO_2$ Rutile, 99%, 20-40 nm, coated with $SiO_2$, highly hydrophobic
$TiO_2$ Rutile, 99%, 20-40 nm, coated with $SiO_2/Al_2O_3$
$TiO_2$ Rutile, 99%, 20-40 nm, coated with $Al_2O_3$, hydrophilic
$TiO_2$ Rutile, 99%, 20-40 nm, coated with $SiO_2/Al_2O_3$/Stearic Acid
$TiO_2$ Rutile, 99%, 20-40 nm, coated with Silicone Oil, hydrophobic
TiC, 99%, 40 nm
TiN, 97+%, 20 nm
$WO_3$, 99.5%, <100 nm
$WS_2$, 99.9%, 0.8 μm
$WCl_6$, 99.0%
$Y_2O_3$, 99.995%, 30-50 nm
ZnO, 99.8%, 10-30 nm
ZnO, 99%, 10-30 nm, treated with silane coupling agents
ZnO, 99%, 10-30 nm, treated with stearic acid
ZnO, 99%, 10-30 nm, treated with silicone oil
ZnO, 99.8%, 200 nm
$ZrO_2$, 99.9%, 100 nm
$ZrO_2$, 99.9%, 20-30 nm
$ZrO_2$-3Y, 99.9%, 0.3-0.5 um
$ZrO_2$-3Y, 25 nm
$ZrO_2$-5Y, 20-30 nm
$ZrO_2$-8Y, 99.9%, 0.3-0.5 μm
$ZrO_2$-8Y, 20 nm
ZrC, 97+%, 60 nm In one aspect, the filler is nanosilica. Nanosilica is commercially available from multiple sources in a broad size range. For example, aqueous Nexsil colloidal silica is available in diameters from 6-85 nm from Nyacol Nanotechnologies, Inc. Amino-modified nanosilica is also commercially available, from Sigma Aldrich for example, but in a narrower range of diameters than unmodified silica. Nanosilica does not contribute to the opacity of the coacervate, which is an important attribute of the adhesives and glues produced therefrom.

In another aspect, the filler can be composed of calcium phosphate. In one aspect, the filler can be hydroxyapatite, which has the formula $Ca_5(PO_4)_3OH$. In another aspect, the filler can be a substituted hydroxyapatite. A substituted hydroxyapatite is hydroxyapatite with one or more atoms substituted with another atom. The substituted hydroxyapatite is depicted by the formula $M_5X_3Y$, where M is Ca, Mg, Na; X is $PO_4$ or $CO_3$; and Y is OH, F, Cl, or $CO_3$. Minor impurities in the hydroxyapatite structure may also be present from the following ions: Zn, Sr, Al, Pb, Ba. In another aspect, the calcium phosphate comprises a calcium orthophosphate. Examples of calcium orthophosphates include, but are not limited to, monocalcium phosphate anhydrate, monocalcium phosphate monohydrate, dicalcium phosphate dihydrate, dicalcium phosphate anhydrous, octacalcium phosphate, beta tricalcium phosphate, alpha tricalcium phosphate, super alpha tricalcium phosphate, tetracalcium phosphate, amorphous tricalcium phosphate, or any combination thereof. In other aspects, the calcium phosphate can also include calcium-deficient hydroxyapatite, which can preferentially adsorb bone matrix proteins.

In certain aspects, the filler can be functionalized with one or more amino or activated ester groups. In this aspect, the filler can be covalently attached to the polycation or polyanion. For example, aminated silica can be reacted with the polyanion possessing activated ester groups to form new covalent bonds.

In other aspects, the filler can be modified to produce charged groups such that the filler can form electrostatic bonds with the coacervates. For example, aminated silica can be added to a solution and the pH adjusted so that the amino groups are protonated and available for electrostatic bonding.

In one aspect, the reinforcing component can be micelles or liposomes. In general, the micelles and liposomes used in this aspect are different from the micelles or liposomes used as polycations and polyanions for preparing the coacervate. The micelles and liposomes can be prepared from the nonionic, cationic, or anionic surfactants described above. The charge of the micelles and liposomes can vary depending upon the selection of the polycation or polyanion as well as the intended use of the coacervate. In one aspect, the micelles and liposomes can be used to solubilize hydrophobic compounds such pharmaceutical compounds. Thus, in addition to be used as adhesives, the adhesive complex coacervates described herein can be effective as a bioactive delivery device.

VIII. Initiators

In certain aspects, the in situ solidifying complex coacervate also includes one or more initiators entrapped in the coacervate. Examples of initiators useful herein include a thermal initiator, a chemical initiator, or a photoinitiator to promote crosslinking amongst the different components in the complex coacervate composition.

Examples of photoinitiators include, but are not limited to a phosphine oxide, peroxides, peracids, azide compounds, α-hydroxyketones, or α-aminoketones. In one aspect, the photoinitiator includes, but is not limited to, camphorquinone, benzoin methyl ether, 1-hydroxycyclohexylphenyl ketone, or Darocure® or Irgacure® types, for example Darocure® 1173 or Irgacure® 2959. The photoinitiators disclosed in European Patent No. 0632329, which are incorporated by reference, can be used herein. In other aspects, the photoinitiator is a water-soluble photoinitiator including, but not limited to, riboflavin, eosin, eosin y, and rose Bengal.

In one aspect, the initiator has a positively charged functional group. Examples include 2,2'-azobis[2-(5-methyl-2-imidazolin-2-yl)propane]-dihydrochloride; 2,2'-azobis[2-(2-imidazolin-2-yl) propane]dihydrochloride; 2,2'-azobis[2-(2-imidazo-lin-2-yl)propane]disulfate dehydrate; 2,2'-azobis(2-methylpropionamidine)dihydrochloride; 2,2'-azobis[2-(3,4,5,6-tetrahydropyrimidin-2-yl)propane]dihydrochloride; azobis{2-[1-(2-hydroxyethyl)-2-imidazolin-2-yl]propane}dihydrochloride; 2,2'-azobis(1-imino-1-pyrrolidino-2-ethylpropane)dihydrochloride and combinations thereof.

In another aspect, the initiator is an oil soluble initiator. In one aspect, the oil soluble initiator includes organic peroxides or azo compounds. Examples of organic peroxides include ketone peroxides, peroxyketals, hydroperoxides, dialkyl peroxides, diacyl peroxides, peroxydicarbonates, peroxyesters, and the like. Some specific non-limiting examples of organic peroxides that can be used as the oil soluble initiator include: lauroyl peroxide, 1,1-bis(t-hexylperoxy)-3,3,5-trimethylcyclohexane, 1,1-bis(t-butylperoxy)-3,3,5-trimethylcyclohexane, t-butylperoxylaurate, t-butylperoxyisopropylmonocarbonate, t-butylperoxy-2-ethylhexylcarbonate, di-t-butylperoxyhexahydroterephthalate, dicumyl peroxide, 2,5-dimethyl-2,5-di(t-butylperoxy)hexane, di-t-butyl peroxide, t-butylperoxy-2-ethylhexanoate, bis(4-t-butylcyclohexyl)peroxydicarbonate, t-amylperoxy-3,5,5-trimethylhexanoate, 1,1-di(t-amylperoxy)-3,3,5-trimethylcyclohexane, benzoylperoxide, t-butylperoxyacetate, and the like.

Some specific non-limiting examples of azo compounds that can be used as the oil soluble initiator include: 2,2'-azobis-isobutyronitrile, 2,2'-azobis-2,4-dimethylvaleronitrile, 1,1'-azobis-1-cyclohexane-carbonitrile, dimethyl-2,2'-azobisisobutyrate, 1,1'-azobis-(1-acetoxy-1-phenylethane), 4,4'-azobis(4-cyanopentanoic acid) and its soluble salts (e.g., sodium, potassium), and the like.

In one aspect, the initiator is a water-soluble initiator including, but not limited to, potassium persulfate, ammonium persulfate, sodium persulfate, and mixtures thereof. In another aspect, the initiator is an oxidation-reduction initiator such as the reaction product of the above-mentioned persulfates and reducing agents such as sodium metabisulfite and sodium bisulfite; and 4,4'-azobis(4-cyanopentanoic acid) and its soluble salts (e.g., sodium, potassium).

In certain aspects, multiple initiators can be used to broaden the absorption profile of the initiator system in order to increase the initiation rate. For example, two different photoinitiators can be employed that are activated by different wavelengths of light. In another aspect, a co-initiator can be used in combination with any of the initiators described herein. In one aspect, the co-initiator is 2-(diethylamino)ethyl acrylate, 2-(dimethylamino)ethyl acrylate, 2-(dimethylamino)ethyl benzoate, 2-(dimethylamino)ethyl methacrylate, 2-ethylhexyl 4-(dimethylamino)benzoate, 3-(dimethylamino)propyl acrylate, 4,4'-bis(diethylamino) benzophenone, or 4-(diethylamino)benzophenone.

In certain aspects, the initiator and/or co-initiator are covalently attached to the polycation and/or polyanion. For example, the initiator and/or co-initiator can be copolymerized with monomers used to make the polycation and/or polyanion. In one aspect, the initiators and co-initiators possess polymerizable olefinic groups such as acrylate and methacrylate groups (e.g., see examples of co-initiators above) that can be copolymerized with monomers described above used to make the polycation and polyanion. In another aspect, the initiators can be chemically grafted onto the backbone of the polycation and polyanion. Thus, in these aspects, the photoinitiator and/or co-initiator are covalently attached to the polymer and pendant to the polymer backbone. This approach will simply formulation and possibly enhance storage and stability.

In other aspects, the initiator and/or co-initiator are electrostatically associated into the fluid complex coacervate.

IX. Multivalent Cations

The in situ solidifying complex coacervates can optionally contain one or more multivalent cations (i.e., cations having a charge of +2 or greater). In one aspect, the multivalent cation can be a divalent cation composed of one or more alkaline earth metals. For example, the divalent cation can be a mixture of $Ca^{+2}$ and $Mg^{+2}$. In other aspects, transition metal ions with a charge of +2 or greater can be used as the multivalent cation. The concentration of the multivalent cations can determine the rate and extent of coacervate formation. Not wishing to be bound by theory, weak cohesive forces between particles in the fluid may be mediated by multivalent cations bridging excess negative surface charges. The amount of multivalent cation used herein can vary. In one aspect, the amount is based upon the number of anionic groups and cationic groups present in the polyanion and polycation.

X. Embolic Agents

As discussed above, the fluid complex coacervates can be used as synthetic embolic agents. However, in other aspects, the fluid complex coacervate described herein can include one or more additional embolic agents. Embolic agents commercially-available are microparticles used for embolization of blood vessels. The size and shape of the microparticles can vary. In one aspect, the microparticles can be composed of polymeric materials. An example of this is Bearin™ nsPVA particles manufactured by Merit Medical Systems, Inc., which are composed of polyvinyl alcohol ranging is size from 45 μm to 1,180 μm. In another aspect, the embolic agent can be a microsphere composed of a polymeric material. Examples of such embolic agents include Embosphere® Microspheres, which are made from trisacryl cross linked with gelatin ranging is size from 40 μm to 1,200 μm; HepaSphere™ Microspheres (spherical, hydrophilic microspheres made from vinyl acetate and methyl acrylate) ranging is size from 30 μm to 200 μm; and QuadraSphere® Microspheres (spherical, hydrophilic microspheres made from vinyl acetate and methyl acrylate) ranging is size from 30 μm to 200 μm, all of which are manufactured by Merit Medical Systems, Inc. In another aspect, the microsphere can be impregnated with one or more metals that can be used as a contrast agent. An example of this is EmboGold® Microspheres manufactured by Merit Medical Systems, Inc., which are made from trisacryl cross linked with gelatin impregnated with 2% elemental gold ranging is size from 40 µm to 1,200 µm.

Preparation of In Situ Solidifying Complex Coacervates

The synthesis of the in situ solidifying complex coacervates described herein can be performed using a number of techniques and procedures. Exemplary techniques for producing the coacervates are provided in international published application no. WO 2016/011028, which is incorporated by reference in its entirety. In one aspect, the polycation and polyanion are mixed as dilute solutions. Upon mixing, when the polycation and polyanion associate they condense into a fluid/liquid phase at the bottom of a mixing chamber (e.g., a tube) to produce a condensed phase. The condensed phase (i.e., fluid complex coacervate) is separated and used as the in situ solidifying complex coacervate.

In one aspect, an aqueous solution of polycation is mixed with an aqueous solution of polyanion such that the positive/negative charge ratio of the polycation to the polyanion is from 4 to 0.25, 3 to 0.25, 2 to 0.25, 1.5 to 0.5, 1.10 to 0.95, 1 to 1. Depending upon the number of charged groups on the polycation and polyanion, the amount of polycation and polyanion can be varied in order to achieve specific positive/negative charge ratios. The in situ solidifying complex coacervate contains water, wherein the amount of water is from 20% to 80% by weight of the composition.

The pH of the solution containing the polycation, polyanion, and the monovalent salt can vary in order to optimize complex coacervate formation. In one aspect, the pH of the composition containing the in situ solidifying complex coacervate is from 6 to 9, 6.5 to 8.5, 7 to 8, or 7 to 7.5. In another aspect, the pH of the composition is 7.2 (i.e., physiological pH).

The amount of the monovalent salt that is present in the in situ solidifying complex coacervate can vary depending upon the concentration of the monovalent salt in the environment at which the in situ solidifying complex coacervate is introduced. In general, the concentration of the monovalent salt in the complex coacervate is greater than the concentration of the monovalent salt in the environment. For example, the concentration of Na and KCl under physiological conditions is about 150 mM. Therefore, if the in situ solidifying complex coacervate is to be administered to a human subject, the concentration of the monovalent salt present in the in situ solidifying complex coacervate would be greater than 150 mM. In one aspect, the monovalent salt that is present in the in situ solidifying complex coacervate is at a concentration from 0.5 M to 2.0 M. In another aspect, the concentration of the monovalent salt is 0.5 to 1.8, 0.5 to 1.6, 0.5 to 1.4, or 0.5 to 1.2. In another aspect, the concentration of the monovalent salt in the complex coacervate is 1.5 to 2, 1.5 to 3, 1.5 to 4, 1.5 to 5, 1.5 to 6, 1.5 to 7, 1.5 to 8, 1.5 to 9 or 1.5 to 10 times greater than the concentration of the monovalent salt in the aqueous environment.

Kits

The polycations and polyanions described herein can be stored as dry powders for extended periods of time. This feature is very useful for preparing the coacervates and ultimately the adhesives when desired.

In one aspect, a kit comprises
(a) a first catheter and a second catheter;
(b) at least one polycation and at least one polyanion, wherein the positive/negative charge ratio of the polycation to the polyanion is from 0.5 to 1.5; and
(c) a salt that produces ions in water at a concentration from 0.5 M to 2.0 M.

In another aspect, the kit comprises
(a) a catheter comprising a first lumen and a second lumen, and wherein the catheter comprises an outer first aperture from the first lumen;
(b) at least one polycation and at least one polyanion, wherein the positive/negative charge ratio of the polycation to the polyanion is from 0.5 to 1.5; and
(c) a salt that produces ions in water at a concentration from 0.5 M to 2.0 M.

When stored as dried powders, water can be added to the polycation and/or polyanion to produce the coacervate. Any of the polyanions, polycations, and salts that produce ions in water can be used in the kits. In one aspect, prior to lyophilizing the polycation and polyanion in order to produce a dry powder, the pH of the polycation and polyanion can be adjusted such that when they are admixed in water the desired pH is produced without the addition of acid or base. For example, excess base can be present in the polycation powder which upon addition of water adjusts the pH accordingly.

The kits can also include additional components as described herein (e.g., reinforcing components, initiators, bioactive agents, contrast agents, etc.).

Exemplary Aspects

Aspect (1) involves a method for anchoring a catheter in a blood vessel of a subject, the method comprising
(a) inserting into a blood vessel of a subject a first catheter and a second catheter, wherein the second catheter is extended further into the vessel than the first catheter; and
(b) injecting into the first catheter an in situ solidifying complex coacervate to produce an adhesive in the vessel that adheres the second catheter to the inner wall of the vessel, wherein the in situ solidifying complex coacervate comprises at least one polycation, at least one polyanion, and a salt that produces ions in water, wherein the concentration of the ions in the complex coacervate is greater than the concentration of the ions in the blood vessel.

Aspect (2) pertains to the method of aspect (1), wherein the first catheter and second catheter are a co-axial catheter.

Aspect (3) pertains to the method of aspect (1), wherein the second catheter comprises an occlusion balloon catheter.

Aspect (4) pertains to the method of aspect (1), wherein the first catheter and second catheter are sistered to one another.

Aspect (5) pertains to the method of aspect (4), wherein the diameter of the first catheter is greater than the diameter of the second catheter.

Aspect (6) pertains to the method of aspect (5), wherein the tip of the second catheter extends past the tip of the first catheter.

Aspect (7) pertains to the method of aspect (1), wherein the adhesive completely seals the vessel.

Aspect (8) pertains to the method of aspect (1), wherein the first catheter is removed from the vessel.

Aspect (9) pertains to the method of aspect (1), wherein the second catheter is removed and the resulting hole in is filled with additional in situ solidifying complex coacervate to produce an embolus.

Aspect (10) pertains to the method of aspect (1), further comprising injecting a bioactive agent in the second catheter.

Aspect (11) pertains to a method for anchoring a catheter in a blood vessel of a subject, the method comprising
  (a) inserting into a blood vessel of a subject a catheter, wherein the catheter comprises a first lumen and a second lumen, and wherein the catheter comprises an outer first aperture from the first lumen; and
  (b) injecting into the first lumen of the catheter an in situ solidifying complex coacervate to produce an adhesive in the vessel that adheres the catheter to the inner wall of the vessel, wherein the in situ solidifying complex coacervate comprises at least one polycation, at least one polyanion, and a salt that produces ions in water, wherein the concentration of the ions in the complex coacervate is greater than the concentration of the ions in the blood vessel.

Aspect (12) pertains to the method of aspect (11), wherein the adhesive completely seals the vessel.

Aspect (13) pertains to the method of aspect (11), wherein the catheter is removed and the resulting hole in is filled with additional in situ solidifying complex coacervate to produce an embolus.

Aspect (14) pertains to the method of aspect (11), further comprising injecting a bioactive agent in the second lumen of the catheter.

Aspect (15) pertains to the method of aspects (1) or (11), wherein the concentration of the ions in the complex coacervate is 1.5 to 10 times greater than the concentration of the ions present in the blood in the blood vessel.

Aspect (16) pertains to the method of aspects (1), (11), or (15), wherein the salt that produces ions comprises a monovalent salt.

Aspect (17) pertains to the method of aspect (16), wherein the monovalent salt comprises sodium chloride, sodium acetate, sodium carbonate, or any combination thereof.

Aspect (18) pertains to the method of aspect (16), wherein the monovalent salt is sodium chloride.

Aspect (19) pertains to the method of aspects (1), (11), or (15), wherein the salt that produces zwitterions.

Aspect (20) pertains to the method of aspect (19), wherein the salt comprises an amino acid or a salt thereof.

Aspect (21) pertains to the method of aspects (1), (11), or (15), wherein the salt that produces ions comprises a multivalent salt.

Aspect (22) pertains to the method of aspects (1) or (11), wherein the total positive/negative charge ratio of the polycation solution to the polyanion is from 4 to 0.25 and the concentration of the ions in the complex coacervate is from 0.5 M to 2.0 M Aspect (23) pertains to the method of aspects (1) or (11), wherein the complex coacervate has a pH of 7 to 7.5.

Aspect (24) pertains to the method of aspects (1) or (11), wherein the polycation comprises a compound with two or more amine groups.

Aspect (25) pertains to the method of aspects (1) or (11), wherein the polycation comprises a biodegradable polyamine.

Aspect (26) pertains to the method of aspect (25), wherein the biodegradable polyamine comprises a polysaccharide, a protein, a recombinant protein, or a synthetic polyamine.

Aspect (27) pertains to the method of aspect (25), wherein the biodegradable polyamine comprises an amine-modified natural polymer.

Aspect (28) pertains to the method of aspects (1) or (11), wherein the polycation comprises a polyacrylate comprising two or more pendant amino groups.

Aspect (29) pertains to the method of aspect (28), wherein the amino group comprises an alkylamino group, (2) a heteroaryl group, a guanidinyl group, an imidazole, or an aromatic group substituted with one or more amino groups, a primary amino group, a secondary amino group, tertiary amino group, or a quaternary amine.

Aspect (30) pertains to the method of aspects (1) or (11), wherein the polycation is a protamine.

Aspect (31) pertains to the method of aspects (1) or (11), wherein the polycation is salmine or clupein.

Aspect (32) pertains to the method of aspects (1) or (11), wherein the polycation is a natural polymer or a synthetic polymer containing two or more guanidinyl sidechains.

Aspect (33) pertains to the method of aspects (1) or (11), wherein the polycation is synthetic polyguanidinyl polymer comprising an acrylate or methacrylate backbone and two or more guanidinyl sidechains.

Aspect (34) pertains to the method of aspects (1) or (11), wherein the polyanion comprises two or more carboxylate, sulfate, sulfonate, borate, boronate, phosphonate, or phosphate groups.

Aspect (35) pertains to the method of aspects (1) or (11), wherein the polyanion comprises a polyphosphate.

Aspect (36) pertains to the method of aspect (35), wherein the polyphosphate comprises a natural polymer or a synthetic polymer.

Aspect (37) pertains to the method of aspect (35), wherein the polyphosphate comprises a polyphosphoserine.

Aspect (38) pertains to the method of aspect (35), wherein the polyphosphate comprises a polyacrylate comprising two or more pendant phosphate groups.

Aspect (39) pertains to the method of aspect (35), wherein the polyphosphate is the copolymerization product between a phosphate acrylate and/or phosphate methacrylate with one or more additional polymerizable monomers.

Aspect (40) pertains to the method of aspect (35), wherein the polyphosphate has from 3-10 phosphate groups.

Aspect (41) pertains to the method of aspect (35), wherein the polyphosphate is an inorganic polyphosphate or a phosphorylated sugar.

Aspect (42) pertains to the method of aspect (35), wherein the polyphosphate is inositol hexaphosphate.

Aspect (43) pertains to the method of aspect (35), wherein the polyphosphate is a hexametaphosphate salt.

Aspect (44) pertains to the method of aspect (35), wherein the polyphosphate is sodium hexametaphosphate.

Aspect (45) pertains to the method of aspects (1) or (11), wherein the polycation and/or polyanion comprises at least one crosslinkable group.

Aspect (46) pertains to the method of aspects (1) or (11), wherein the complex coacervate further comprises a contrast agent or a visualization agent.

Aspect (47) pertains to the method of aspect (46), wherein the contrast agent comprises tantalum particles, gold particles, or iodine.

Aspect (48) pertains to the method of aspects (1) or (11), wherein the complex coacervate further comprises a reinforcing component.

Aspect (49) pertains to the method of aspect (48), wherein the reinforcing component comprises a natural or synthetic fiber, polymerizable monomer, water-insoluble filler, a nanostructure, a micelle, or a liposome.

Aspect (50) pertains to the method of aspect (49), wherein the reinforcing component comprises a filler, and the filler comprises a metal oxide, a ceramic particle, or a water insoluble inorganic salt.

Aspect (51) pertains to the method of aspects (1) or (11), wherein the coacervate further comprises one or more bioactive agents encapsulated in the coacervate.

Aspect (52) pertains to the method of aspect (50), wherein the bioactive agent comprises a nucleic acid, an antibiotic, a pain reliever, an anti-inflammatory agent, an immune modulator, a growth factor, an enzyme inhibitor, a hormone, a mediator, a messenger molecule, a cell signaling molecule, a receptor agonist, an oncolytic, a chemotherapy agent, a receptor antagonist, a MAB fragment, a monoclonal antibodies, an anti-angiogenic agent, or any combination thereof.

Aspect (53) pertains to the method of aspect (51), wherein the bioactive agent is an anti-angiogenic agent.

Aspect (54) pertains to the method of aspect (53), wherein the anti-angiogenic agent comprises a tyrosine kinase inhibitor.

Aspect (55) pertains to the method of aspect (54), wherein the tyrosine kinase inhibitor comprises sunitinib malate, pazopanib hydrochloride, sorafenib tosylate, vandetanib, cabozantinib, or any combination thereof.

Aspect (56) pertains to the method of aspect (53), wherein the anti-angiogenic agent comprises an anti-VEGF antibody.

Aspect (57) pertains to the method of aspect (56), wherein the anti-VEGF antibody is bevacizumab.

Aspect (58) pertains to the method of aspect (53), wherein the amount of anti-angiogenic agent is from 1 mg/mL to 100 mg/mL of the in situ solidifying liquid complex coacervate.

Aspect (59) pertains to the method of aspect (51), wherein the bioactive agent comprises a water-soluble chemotherapeutic agent.

Aspect (60) pertains to the method of aspect (59), wherein the bioactive agent is doxorubicin.

Aspect (61) pertains to the method of aspect (51), wherein the bioactive agent comprises an anti-inflammatory agent.

Aspect (62) pertains to the method of aspect (61), wherein the anti-inflammatory agent comprises an NSAID, a COX-2 inhibitor, a corticosteroid, or any combination thereof.

Aspect (63) pertains to the method of aspects (1) or (11), wherein the polycation is a polyguanidinyl copolymer comprising the polymerization product between a monomer selected from the group consisting of an acrylate, a methacrylate, an acrylamide, a methacrylamide, or any combination thereof and a compound of formula XX

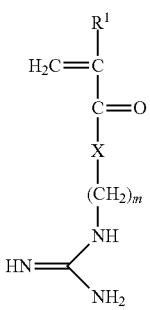

XX wherein $R^1$ is hydrogen or an alkyl group, X is oxygen or $NR^5$, where $R^5$ is hydrogen or an alkyl group, and m is from 1 to 10, or the pharmaceutically-acceptable salt thereof, the mole ratio of the compound of formula I to the monomer is from 1:1 to 10:1,
the polyguanidinyl copolymer has a molar mass from 5 kg/mol to 80 kg/mol, and
the charge ratio of polyguanidinyl copolymer to polyphosphate is from 0.5:1 to 1.5:1.

Aspect (64) pertains to the method of aspect (63), wherein $R^1$ is methyl, X is NH, and m is 3.

Aspect (65) pertains to the method of aspect (63), wherein the monomer is methacrylamide.

Aspect (66) pertains to the method of aspect (63), wherein the mole ratio of the compound of formula I to the monomer is from 3:1 to 5:1.

Aspect (67) pertains to the method of aspect (63), wherein the molecular weight distribution of the polyguanidinyl copolymer is distributed around an average molecular weight between 5 kDa to 100 kDa.

Aspect (68) pertains to the method of aspect (63), wherein the polyguanidinyl copolymer comprises a multimodal distribution of polyguanidinyl copolymer molecular weights with modes between 5 and 100 kDa.

Aspect (69) pertains to the method of aspect (63), wherein the polyanion comprises a hexametaphosphate salt.

Aspect (70) pertains to the method of aspect (63), wherein the polyanion is sodium hexametaphosphate.

Aspect (71) pertains to the method of aspect (63), wherein the polyanion is inositol hexaphosphate.

Aspect (72) pertains to the method of aspect (63), wherein the salt in the complex coacervate is NaCl at a concentration of 1.5 to 10 times greater than the concentration of the monovalent ions in the subject.

Aspect (73) pertains to the method of aspect (63), wherein the charge ratio of polyguanidinyl copolymer to polyanion is from 0.95:1 to 1.05:1.

Aspect (74) pertains to the method of aspect (63), wherein the coacervate further comprises one or more bioactive agents encapsulated in the coacervate, Aspect (75) pertains to the method of aspect (74), wherein the bioactive agent comprises a nucleic acid, an antibiotic, a pain reliever, an immune modulator, a growth factor, an enzyme inhibitor, a hormone, a mediator, a messenger molecule, a cell signaling molecule, a receptor agonist, an oncolytic, a chemotherapy agent, a receptor antagonist, a MAB fragment, a monoclonal antibodies, an anti-angiogenic agent, or any combination thereof.

Aspect (76) pertains to the method of aspect (74), wherein the bioactive agent is an anti-angiogenic agent.

Aspect (77) pertains to the method of aspect (76), wherein the anti-angiogenic agent comprises a tyrosine kinase inhibitor.

Aspect (78) pertains to the method of aspect (77), wherein the tyrosine kinase inhibitor comprises sunitinib malate, pazopanib hydrochloride, sorafenib tosylate, vandetanib, cabozantinib, or any combination thereof.

Aspect (79) pertains to the method of aspect (76), wherein the anti-angiogenic agent comprises an anti-VEGF antibody.

Aspect (80) pertains to the method of aspect (79), wherein the anti-VEGF antibody is bevacizumab.

Aspect (81) pertains to the method of aspect (76), wherein the amount of anti-angiogenic agent is from 1 mg/mL to 100 mg/mL of the in situ solidifying liquid complex coacervate.

Aspect (82) pertains to the method of aspect (74), wherein the bioactive agent comprises a water-soluble chemotherapeutic agent.

Aspect (83) pertains to the method of aspect (82), wherein the bioactive agent is doxorubicin.

Aspect (84) pertains to the method of aspect (74), wherein the bioactive agent comprises an anti-inflammatory agent.

Aspect (85) pertains to the method of aspect (84), wherein the anti-inflammatory agent comprises an NSAID, a COX-2 inhibitor, a corticosteroid, or any combination thereof.

Aspect (86) pertains to the method of aspect (63), wherein the in situ solidifying liquid complex coacervate has a pH of 7 to 7.5.

Aspect (87) pertains to the method of aspect (63), wherein the in situ solidifying liquid complex coacervate further comprises a contrast agent or a visualization agent.

Aspect (88) pertains to the method of aspect (87), wherein the contrast agent comprises tantalum particles, gold particles, or iodine.

Aspect (89) pertains to the method of aspect (63), wherein the in situ solidifying liquid complex coacervate further comprises a reinforcing component.

Aspect (90) pertains to the method of aspect (89), wherein the reinforcing component comprises a coil or fiber.

Aspect (91) pertains to the method of aspect (89), wherein the reinforcing component comprises a natural or synthetic fiber, polymerizable monomer, water-insoluble filler, a nanostructure, a micelle, or a liposome.

Aspect (92) pertains to the method of aspect (89), wherein the reinforcing component comprises a filler, and the filler comprises a metal oxide, a ceramic particle, or a water insoluble inorganic salt.

Aspect (93) pertains to the method of aspect (63), wherein the salt that produces ions comprises a monovalent salt.

Aspect (94) pertains to the method of aspect (93), wherein the monovalent salt comprises sodium chloride, sodium acetate, sodium carbonate, or any combination thereof.

Aspect (95) pertains to the method of aspect (93), wherein the monovalent salt is sodium chloride.

Aspect (96) pertains to the method of aspects (1) or (11), wherein the anchored catheter reduces or inhibits blood flow to an aneurysm, a varicose vein, or an arteriovenous malformation.

Aspect (97) pertains to the method of aspects (1) or (11), wherein the subject is a mammal.

Aspect (98) pertains to the method of aspects (1) or (11), wherein the subject has a tumor.

Aspect (99) pertains a kit comprising
(a) a first catheter and a second catheter;
(b) at least one polycation and at least one polyanion, wherein the positive/negative charge ratio of the polycation to the polyanion is from 0.5 to 1.5; and
(c) a salt that produces ions in water at a concentration from 0.5 M to 2.0 M.

Aspect (100) pertains to the kit of aspect (99), wherein the first catheter and second catheter are a co-axial catheter.

Aspect (101) pertains to the kit of aspect (99), wherein the second catheter comprises an occlusion balloon catheter.

Aspect (102) pertains to the kit of aspect (99), wherein the first catheter and second catheter are sistered to one another.

Aspect (103) pertains to the kit of aspect (102), wherein the diameter of the first catheter is greater than the diameter of the second catheter.

Aspect (104) pertains to a kit comprising
(a) a catheter comprising a first lumen and a second lumen, and wherein the catheter comprises an outer first aperture from the first lumen;
(b) at least one polycation and at least one polyanion, wherein the positive/negative charge ratio of the polycation to the polyanion is from 0.5 to 1.5; and
(c) a salt that produces ions in water at a concentration from 0.5 M to 2.0 M.

Aspect (105) pertains to the kit of aspects (99) or (104), wherein the salt that produces ions comprises a monovalent salt.

Aspect (106) pertains to the kit of aspect (105), wherein the monovalent salt comprises sodium chloride, sodium acetate, sodium carbonate, or any combination thereof.

Aspect (107) pertains to the kit of aspect (105), wherein the monovalent salt is sodium chloride.

Aspect (108) pertains to the kit of aspects (99) or (104), wherein the salt that produces zwitterions.

Aspect (109) pertains to the kit of aspect (108), wherein the salt comprises an amino acid or a salt thereof.

Aspect (110) pertains to the kit of aspects (99) or (104), wherein the salt that produces ions comprises a multivalent salt.

Aspect (111) pertains to the kit of aspects (99) or (104), wherein the polycation comprises a compound with two or more amine groups.

Aspect (112) pertains to the kit of aspects (99) or (104), wherein the polycation comprises a biodegradable polyamine.

Aspect (113) pertains to the kit of aspect (112), wherein the biodegradable polyamine comprises a polysaccharide, a protein, a recombinant protein, or a synthetic polyamine.

Aspect (114) pertains to the kit of aspect (112), wherein the biodegradable polyamine comprises an amine-modified natural polymer.

Aspect (115) pertains to the kit of aspects (99) or (104), wherein the polycation comprises a polyacrylate comprising two or more pendant amino groups.

Aspect (116) pertains to the kit of aspect (115), wherein the amino group comprises an alkylamino group, (2) a heteroaryl group, a guanidinyl group, an imidazole, or an aromatic group substituted with one or more amino groups, a primary amino group, a secondary amino group, tertiary amino group, or a quaternary amine.

Aspect (117) pertains to the kit of aspects (99) or (104), wherein the polycation is a protamine.

Aspect (118) pertains to the kit of aspects (99) or (104), wherein the polycation is salmine or clupein.

Aspect (119) pertains to the kit of aspects (99) or (104), wherein the polycation is a natural polymer or a synthetic polymer containing two or more guanidinyl sidechains.

Aspect (120) pertains to the kit of aspects (99) or (104), wherein the polycation is synthetic polyguanidinyl polymer comprising an acrylate or methacrylate backbone and two or more guanidinyl sidechains.

Aspect (121) pertains to the kit of aspects (99) or (104), wherein the polyanion comprises two or more carboxylate, sulfate, sulfonate, borate, boronate, phosphonate, or phosphate groups.

Aspect (122) pertains to the kit of aspects (99) or (104), wherein the polyanion comprises a polyphosphate.

Aspect (123) pertains to the kit of aspect (122), wherein the polyphosphate comprises a natural polymer or a synthetic polymer.

Aspect (124) pertains to the kit of aspect (122), wherein the polyphosphate comprises a polyphosphoserine.

Aspect (125) pertains to the kit of aspect (122), wherein the polyphosphate comprises a polyacrylate comprising two or more pendant phosphate groups.

Aspect (126) pertains to the kit of aspect (122), wherein the polyphosphate is the copolymerization product between a phosphate acrylate and/or phosphate methacrylate with one or more additional polymerizable monomers.

Aspect (127) pertains to the kit of aspect (122), wherein the polyphosphate has from 3-10 phosphate groups.

Aspect (128) pertains to the kit of aspect (122), wherein the polyphosphate is an inorganic polyphosphate or a phosphorylated sugar.

Aspect (129) pertains to the kit of aspect (122), wherein the polyphosphate is inositol hexaphosphate.

Aspect (130) pertains to the kit of aspect (122), wherein the polyphosphate is a hexametaphosphate salt.

Aspect (131) pertains to the kit of aspect (122), wherein the polyphosphate is sodium hexametaphosphate.

Aspect (132) pertains to the kit of aspects (99) or (104), wherein the polycation and/or polyanion comprises at least one crosslinkable group.

Aspect (133) pertains to the kit of aspects (99) or (104), wherein the kit further comprises a contrast agent or a visualization agent.

Aspect (134) pertains to the kit of aspect (133), wherein the contrast agent comprises tantalum particles, gold particles, or iodine.

Aspect (135) pertains to the kit of aspects (99) or (104), wherein the kit further comprises a reinforcing component.

Aspect (136) pertains to the kit of aspect (135), wherein the reinforcing component comprises a natural or synthetic fiber, polymerizable monomer, water-insoluble filler, a nanostructure, a micelle, or a liposome.

Aspect (137) pertains to the kit of aspect (135), wherein the reinforcing component comprises a filler, and the filler comprises a metal oxide, a ceramic particle, or a water insoluble inorganic salt.

Aspect (138) pertains to the kit of aspects (99) or (104), wherein the kit further comprises one or more bioactive agents.

Aspect (139) pertains to the kit of aspect (138), wherein the bioactive agent comprises a nucleic acid, an antibiotic, a pain reliever, an anti-inflammatory agent, an immune modulator, a growth factor, an enzyme inhibitor, a hormone, a mediator, a messenger molecule, a cell signaling molecule, a receptor agonist, an oncolytic, a chemotherapy agent, a receptor antagonist, a MAB fragment, a monoclonal antibodies, an anti-angiogenic agent, or any combination thereof.

Aspect (140) pertains to the kit of aspect (138), wherein the bioactive agent is an anti-angiogenic agent.

Aspect (141) pertains to the kit of aspect (140), wherein the anti-angiogenic agent comprises a tyrosine kinase inhibitor.

Aspect (142) pertains to the kit of aspect (141), wherein the tyrosine kinase inhibitor comprises sunitinib malate, pazopanib hydrochloride, sorafenib tosylate, vandetanib, cabozantinib, or any combination thereof.

Aspect (143) pertains to the kit of aspect (140), wherein the anti-angiogenic agent comprises an anti-VEGF antibody.

Aspect (144) pertains to the kit of aspect (143), wherein the anti-VEGF antibody is bevacizumab.

Aspect (145) pertains to the kit of aspect (138), wherein the bioactive agent comprises a water-soluble chemotherapeutic agent.

Aspect (146) pertains to the kit of aspect (145), wherein the bioactive agent is doxorubicin.

Aspect (147) pertains to the kit of aspect (138), wherein the bioactive agent comprises an anti-inflammatory agent.

Aspect (148) pertains to the kit of aspect (147), wherein the anti-inflammatory agent comprises an NSAID, a COX-2 inhibitor, a corticosteroid, or any combination thereof.

Aspect (149) pertains to the kit of aspects (99) or (104), wherein the polycation is a polyguanidinyl copolymer comprising the polymerization product between a monomer selected from the group consisting of an acrylate, a methacrylate, an acrylamide, a methacrylamide, or any combination thereof and a compound of formula XX

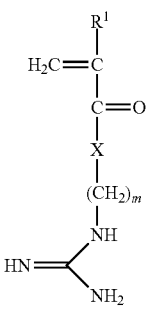

wherein $R^1$ is hydrogen or an alkyl group, X is oxygen or $NR^5$, where $R^5$ is hydrogen or an alkyl group, and m is from 1 to 10, or the pharmaceutically-acceptable salt thereof, the mole ratio of the compound of formula I to the monomer is from 1:1 to 10:1, the polyguanidinyl copolymer has a molar mass from 5 kg/mol to 80 kg/mol, and the charge ratio of polyguanidinyl copolymer to polyphosphate is from 0.5:1 to 1.5:1.

Aspect (150) pertains to the kit of aspect (149), wherein $R^1$ is methyl, X is NH, and m is 3.

Aspect (151) pertains to the kit of aspect (149), wherein the monomer is methacrylamide.

Aspect (152) pertains to the kit of aspect (149), wherein the mole ratio of the compound of formula I to the monomer is from 3:1 to 5:1.

Aspect (153) pertains to the kit of aspect (149), wherein the molecular weight distribution of the polyguanidinyl copolymer is distributed around an average molecular weight between 5 kDa to 100 kDa.

Aspect (154) pertains to the kit of aspect (149), wherein the polyguanidinyl copolymer comprises a multimodal distribution of polyguanidinyl copolymer molecular weights with modes between 5 and 100 kDa.

Aspect (155) pertains to the kit of aspect (149), wherein the polyanion comprises a hexametaphosphate salt.

Aspect (156) pertains to the kit of aspect (149), wherein the polyanion is sodium hexametaphosphate.

Aspect (157) pertains to the kit of aspect (149), wherein the polyanion is inositol hexaphosphate.

Aspect (158) pertains to the kit of aspect (149), wherein the charge ratio of polyguanidinyl copolymer to polyanion is from 0.95:1 to 1.05:1.

Aspect (159) pertains to the kit of aspect (149), wherein the kit further comprises one or more bioactive agents.

Aspect (160) pertains to the kit of aspect (159), wherein the bioactive agent comprises a nucleic acid, an antibiotic, a pain reliever, an immune modulator, a growth factor, an enzyme inhibitor, a hormone, a mediator, a messenger molecule, a cell signaling molecule, a receptor agonist, an oncolytic, a chemotherapy agent, a receptor antagonist, a MAB fragment, a monoclonal antibodies, an anti-angiogenic agent, or any combination thereof.

Aspect (161) pertains to the kit of aspect (159), wherein the bioactive agent is an anti-angiogenic agent.

Aspect (162) pertains to the kit of aspect (161), wherein the anti-angiogenic agent comprises a tyrosine kinase inhibitor.

Aspect (163) pertains to the kit of aspect (162), wherein the tyrosine kinase inhibitor comprises sunitinib malate, pazopanib hydrochloride, sorafenib tosylate, vandetanib, cabozantinib, or any combination thereof.

Aspect (164) pertains to the kit of aspect (161), wherein the anti-angiogenic agent comprises an anti-VEGF antibody.

Aspect (165) pertains to the kit of aspect (164), wherein the anti-VEGF antibody is bevacizumab.

Aspect (166) pertains to the kit of aspect (159), wherein the bioactive agent comprises a water-soluble chemotherapeutic agent.

Aspect (167) pertains to the kit of aspect (166), wherein the bioactive agent is doxorubicin.

Aspect (168) pertains to the kit of aspect (159), wherein the bioactive agent comprises an anti-inflammatory agent.

Aspect (169) pertains to the kit of aspect (167), wherein the anti-inflammatory agent comprises an NSAID, a COX-2 inhibitor, a corticosteroid, or any combination thereof.

Aspect (170) pertains to the kit of aspect (149), wherein the kit further comprises a contrast agent or a visualization agent.

Aspect (171) pertains to the kit of aspect (170), wherein the contrast agent comprises tantalum particles, gold particles, or iodine.

Aspect (172) pertains to the kit of aspect (149), wherein the kit further comprises a reinforcing component.

Aspect (173) pertains to the kit of aspect (172), wherein the reinforcing component comprises a coil or fiber.

Aspect (174) pertains to the kit of aspect (172), wherein the reinforcing component comprises a natural or synthetic fiber, polymerizable monomer, water-insoluble filler, a nanostructure, a micelle, or a liposome.

Aspect (175) pertains to the kit of aspect (172), wherein the reinforcing component comprises a filler, and the filler comprises a metal oxide, a ceramic particle, or a water insoluble inorganic salt.

EXAMPLES

The following examples are put forth so as to provide those of ordinary skill in the art with a complete disclosure and description of how the compounds, compositions, and methods described herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g. component concentrations, desired solvents, solvent mixtures, temperatures, pressures, and other reaction ranges and conditions can be used to optimize the product purity and yield obtained from the described process. Only reasonable and routine experimentation will be required to optimize such process conditions.

Reagents

N-(3-aminopropyl) methacrylamide hydrochloride (APMA) was obtained from Polysciences, Inc. (cat #21200). 1H-Pyrazole-1-Carboxamidine hydrochloride was purchased from Chem-Ipex International (cat #21678). Methacrylamide (MA; L15013) and glacial acetic acid (cat #36289) were obtained from Alfa Aesar. 4-methoxyphenol was purchased from TCI chemicals (cat #M0123). 4,4'-Azobis(4-cyanovaleric acid) (V501; cat #11590) and azobisisobutyronitrile (AIBN; cat #441090) were obtained from Sigma-Aldrich. 4-Cyano-4-(thiobenzoylthio)pentanoic acid was purchased from Strem Chemicals (cat #16-0422). Sodium acetate was obtained from VWR (cat #0602). USP grade sodium chloride (NaCl; cat #102892) was purchased from MP Biosciences. Triethylamine (TEA) was obtained from Fischer Scientific (cat ##BP616-500). Tantalum metal powder (1-5 micron particle size) was purchased from Atlantic Equipment Engineers, Inc. (cat #TA-101). Solutions were made in ultrapure double deionized water.

Synthesis of N-(3-Methacrylamidopropyl) Guanidinium Chloride (GPMA)

A flask was charged with N-(3-aminopropyl) methacrylamide hydrochloride (APMA) (20 g; 112 mmol) and the inhibitor 4-methoxyphenol (0.2 g; 1.6 mmol). DMF (112 mL) was added to dissolve APMA at a concentration of 1 M. TEA (18.7 mL; 134 mmol) was added to the flask and the mixture was stirred for 5 minutes under $N_2$. Next, 1H-pyrazole-1-carboxamidine hydrochloride (16.4 g; 112 mmol) was added. The mixture was reacted at 20° C. under $N_2$. After 16 h, TEA HCl salts were separated from the reaction mixture by vacuum filtration using a Buchner funnel. The monomer was extracted with diethyl ether 3 times, forming a dense oil. Finally, the monomer was collected dried under vacuum. The product was confirmed by proton and carbon NMR. $^1$H NMR (400 MHz, D2O): δ (ppm) 1.68 (q, $CH_2$—$CH_2$—$CH_2$), 1.77 (s, $CH_3$), 3.08 (m, $CH_2$—N), 3.18 (m, $CH_2$—N), 5.30 (s, =$CH_2$), 5.55 (s, =$CH_2$). $^3$C NMR: (400 MHz, D2O) δ (ppm) 17.74 ($CH_3$), 27.62 ($CH_2$), 36.62 ($CH_2$—N), 38.71 ($CH_2$—N), 121.13 (C=$CH_2$), 138.83 ($CH_2$=C), 156.6 2(C), 171.55 (C=O). Formation of GPMA was also verified by ESI mass spectroscopy (185.1 Da).

RAFT Polymerization of GPMA and Methacrylamide (MA)

RAFT polymerization was employed using 4-cyano-4-(thiobenzoylthio)pentanoic acid as the chain transfer agent (CTA) and V-501 as the initiator at a 5:1 molar ratio. A fixed molar ratio of 80:20 (GPMA:MA) and molecular weight of 20 kD were targeted. GPMA (9.12 g, 41 mmol), MA (0.88 g, 10 mmol), 4-cyano-4-(thiobenzoylthio)pentanoic acid (112 mg, 0.400 mmol), and V-501 (22.4 mg; 0.080 mmol) were dissolved in 1 M (pH 5.3) acetate buffer (52 mL). The resulting solution was degassed by bubbling for 2 hours with $N_2$ before being septum sealed. The reaction was kept under $N_2$ while it proceeded at 70° C. for 16 hours. The resulting polymer was cooled, exposed to air, and precipitated in acetone. For end group modification, the polymer was redissolved in methanol (~100 mL), and AIBN (1.3 g, 8 mmol) was added. The solution was degassed and reacted under $N_2$ for 4 hours at 60° C. The product was precipitated in acetone, collected by filtration, and dried under vacuum. A Millipore ultrafiltration system equipped with a Pellicon 2 Minicassette (Biomax® 5 kDa) was used to purify the final product. To convert the polymer to the hydrochloride salt, it was dissolved in DI water and washed with a 20× volume of 150 mM NaCl at pH 3 (adjusted with HCl). Next, an additional 20× volume exchange was performed with DI water. Finally, the purified retentate was freeze dried.

Production of In Situ Solidifying Complex Coacervate

Coacervates of p(GPMA-co-MA) (PG) and sodium hexametaphosphate (MP) were prepared with 1-5 micron Ta powder added as a radiocontrast agent (30 wt % of final coacervate), unless otherwise noted. Aqueous stock solutions of PG and MP were made at 100 mg/mL and 200 mg/mL, respectively. The pH of both solutions was adjusted to 7.2. Coacervation was achieved by sequential addition of DI water, 5M NaCl, MP solution, Ta powder, and PG solution, while mixing with an overhead mixer. In this final mixture, PG concentration was fixed at 50 mg/mL; MP concentration was 42 mg/mL based upon calculated charge densities and a 1:2 charge ratio. Amounts of DI water and 5 M salt were adjusted to form a NaCl concentration of 800 mM. Phase separation occurred immediately upon addition of PG, and the coacervate was allowed to settle for 12 hr. Afterwards, the supernatant was removed and 5 M NaCl was mixed into the condensed phase using trituration to bring the overall NaCl concentration in the coacervate to its final concentration (1400 mM, unless otherwise noted).

Catheter Entrapment Studies

Catheter entrapment is a serious problem that occurs with many clinical embolization agents. The in situ solidifying complex coacervate produced above was evaluated to determine the risk of catheter entrapment. The force required to remove a catheter embedded in the coacervate after 2 min and 24 hrs was measured using an Instron 3342 materials tester (Instron, Inc). Catheters were cleanly detached from the coacervate at 2 min and 24 hrs with no fragmentation or coacervate adhesion with minimal force.

Dual Catheter Studies

A dual-catheter, "buddy-cath" technique to deploy the in situ solidifying coacervate around a microcatheter was investigated in order to (1) occlude the vessel with the coacervate while maintaining access distal to plug, and (2) observe any coacervate adhesion upon removal of the catheter.

Figure 7:
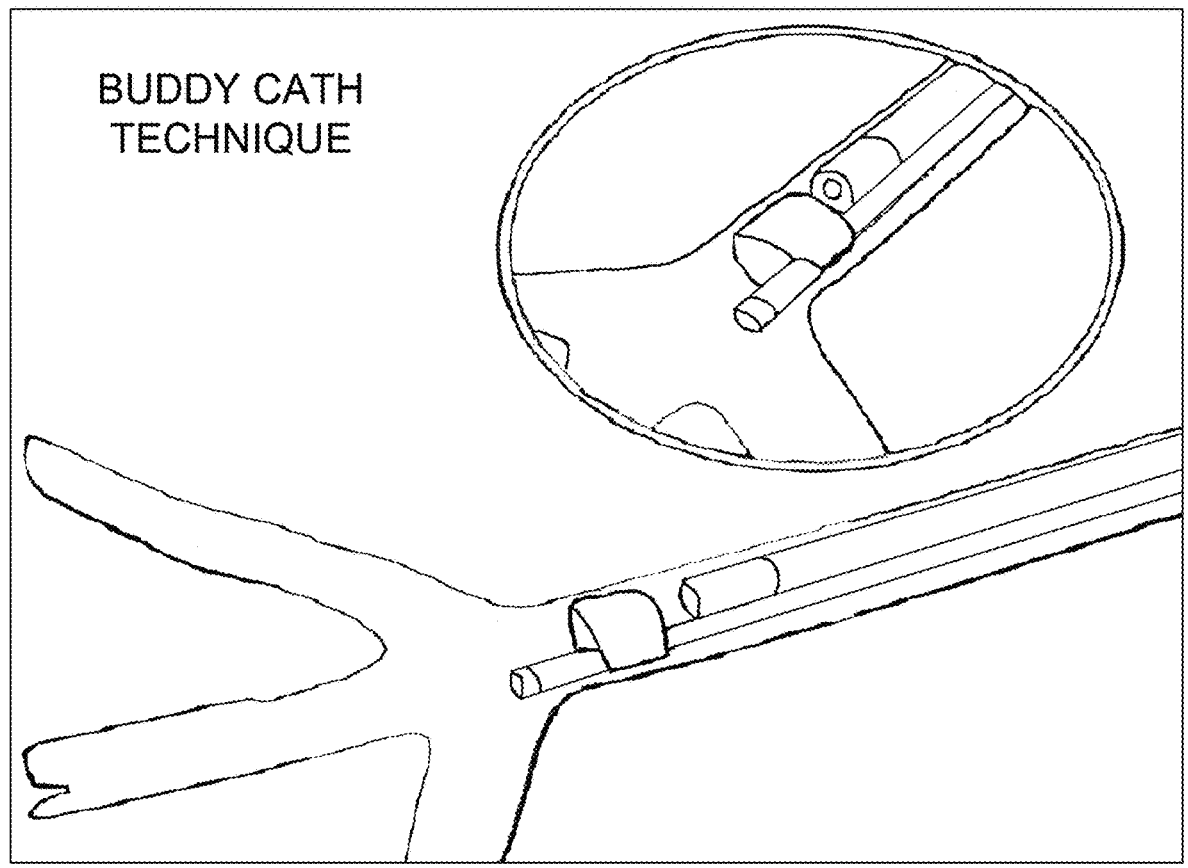
FIG. 7 shows the use of an in situ solidifying complex coacervate in a dual catheter application.
Figure 8:
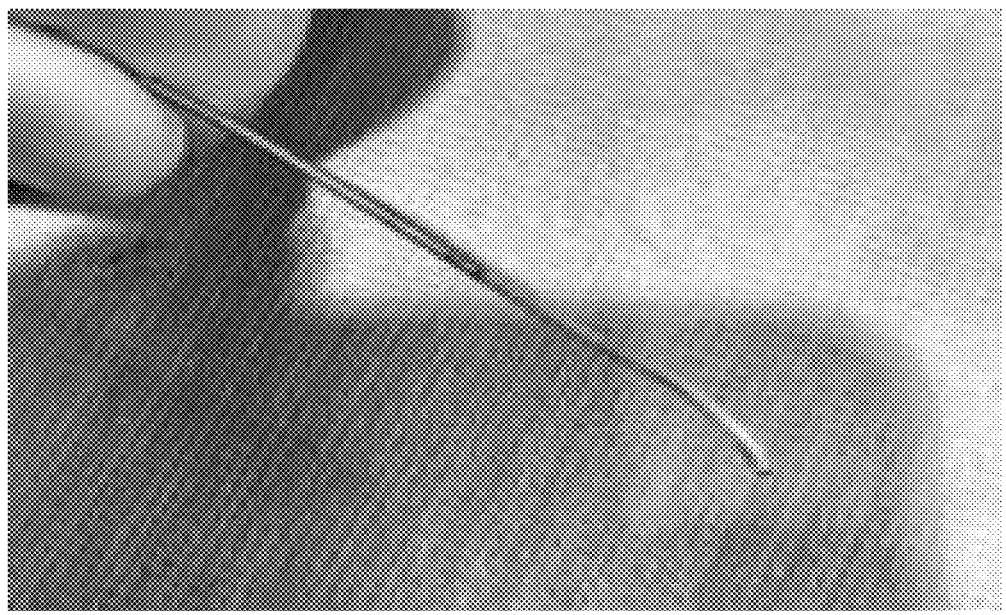
FIG. 8 shows that the use of an in situ solidifying complex coacervate does not adhere to a catheter upon removal of the catheter from a vessel.

In a 50 kg porcine model, the coacervate was deployed through catheter (4F Terumo Glidecath) over microcatheter (2.4F BSC Direxion) to the lower lobe of the right kidney. The coacervate formed plug around microcatheter creating an occlusion (FIG. 7). The microcatheter was left in place for 2 minutes then removed with no evidence of coacervate adhesion to the microcatheter (FIG. 8). The coacervate self-sealed the microcatheter track/lumen upon withdrawal of the microcatheter.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification be considered as exemplary.

What is claimed:

1. A method for anchoring a catheter in a blood vessel of a subject, the method comprising (a) inserting into a blood vessel of a subject a catheter; and (b) injecting into the catheter an injectable composition, wherein the injectable composition comprises water and oppositely charged polyelectrolytes and counterions, wherein the concentration of the counterions in the injectable composition is greater than the concentration of ions in the blood vessel, whereupon introduction of the injectable composition into the blood vessel a solid or gel is produced in situ that seals the catheter to an inner wall of the vessel.

2. The method of claim 1, wherein the catheter comprises a first catheter and a second catheter, wherein the second catheter is extended further into the vessel than the first catheter, wherein the injectable composition is injected into the first catheter, whereupon introduction of the injectable composition into the blood vessel a solid or gel is produced in situ that seals the second catheter to the inner wall of the vessel.

3. The method of claim 2, wherein the first catheter and second catheter are a co-axial catheter.

4. The method of claim 2, wherein the second catheter comprises an occlusion balloon catheter.

5. The method of claim 2, wherein the first catheter and second catheter are sistered to one another.

6. The method of claim 5, wherein the diameter of the first catheter is greater than the diameter of the second catheter.

7. The method of claim 6, wherein a tip of the second catheter extends past a tip of the first catheter.

8. The method of claim 2, wherein the solid or gel completely seals the vessel.

9. The method of claim 2, wherein the first catheter is removed from the vessel.

10. The method of claim 2, wherein the second catheter is removed producing a hole that is filled with additional injectable composition to produce an embolus.

11. The method of claim 1, further comprising injecting a bioactive agent in the second catheter.

12. The method of claim 1, wherein the catheter comprises a first lumen and a second lumen, and wherein the catheter comprises an outer first aperture from the first lumen, wherein the injectable composition is injected into the first lumen and exits the outer first aperture, whereupon introduction of the injectable composition into the blood vessel a solid or gel is produced in situ that seals the catheter to the inner wall of the vessel.

13. The method of claim 12, wherein the gel or solid completely seals the vessel.

14. The method of claim 12, wherein the catheter is removed producing a hole that is filled with additional injectable composition to produce an embolus.

15. The method of claim 12, further comprising injecting a bioactive agent in the second lumen of the catheter.

16. The method of claim 1, wherein the injectable composition further comprises one or more bioactive agents.

17. The method of claim 16, wherein the bioactive agent comprises a nucleic acid, an antibiotic, a pain reliever, an anti-inflammatory agent, an immune modulator, a growth factor, an enzyme inhibitor, a hormone, a mediator, a messenger molecule, a cell signaling molecule, a receptor agonist, an oncolytic, a chemotherapy agent, a receptor antagonist, an antibody fragment, a monoclonal antibody, an anti-angiogenic agent, or any combination thereof.

18. The method of claim 1, wherein the injectable composition further comprises a radiographic contrast agent or a fluoroscopic contrast agent.

19. The method of claim 1, wherein the anchored catheter reduces or inhibits blood flow to a tumor, an aneurysm, a varicose vein, or a vascular malformation.

20. The method of claim 1, wherein the subject has a tumor.

* * * * *